United States Patent [19]

Ong et al.

[11] Patent Number: 4,524,207

[45] Date of Patent: Jun. 18, 1985

[54] PROCESS FOR PREPARING SUBSTITUTED 1,3-DIHYDROSPIRO[BENZO(C)THIOPHENE]S

[75] Inventors: Helen H. Ong, Whippany; Vernon B. Anderson, High Bridge, both of N.J.; James A. Profitt, Goshen, Ind.

[73] Assignee: Hoechst-Roussel Pharmaceuticals Inc., Somerville, N.J.

[21] Appl. No.: 515,969

[22] Filed: Jul. 21, 1983

Related U.S. Application Data

[60] Division of Ser. No. 313,169, Oct. 20, 1981, Pat. No. 4,409,229, which is a continuation-in-part of Ser. No. 165,344, Jul. 2, 1980, abandoned, which is a continuation of Ser. No. 948,908, Oct. 5, 1978, abandoned, which is a continuation-in-part of Ser. No. 857,177, Dec. 2, 1977, abandoned.

[51] Int. Cl.$^3$ .................. C07D 495/10; C07D 513/10
[52] U.S. Cl. ...................................... 546/17; 548/409
[58] Field of Search ........................... 546/17; 548/409

[56] References Cited

U.S. PATENT DOCUMENTS

3,959,475  5/1976  Bauer et al. ............................ 546/17
4,409,229 10/1983  Ong et al. ............................. 546/17

OTHER PUBLICATIONS

Parham et al., "J. Organic Chemistry", vol. 41, pp. 2628–2633 (1976).
Conant, "The Chemistry of Organic Compounds", MacMillan (1947), p. 264.

*Primary Examiner*—Robert T. Bond
*Attorney, Agent, or Firm*—Curtis, Morris & Safford

[57] ABSTRACT

Novel substituted 1,3-dihydrospiro[benzo(c)thiophene]s and methods of preparing the same are described. These compounds are useful as antidepressants and tranquilizers and intermediates therefor.

1 Claim, No Drawings

PROCESS FOR PREPARING SUBSTITUTED 1,3-DIHYDROSPIRO[BENZO(C)THIOPHENE]S

This is a division of application Ser. No. 313,169 filed Oct. 20, 1981 now U.S. Pat. No. 4,409,229, which is a continuation-in-part of Ser. No. 165,344, filed 7/2/80, now abandoned, which is a continuation of Ser. No. 948,908 filed 10/5/78 now abandoned, which in turn is a continuation-in-part of Ser. No. 857,177 filed 12/2/77, now abandoned.

This invention relates to novel substituted 1,3-dihydrospiro[benzo(c)thiophene]s which are useful as antidepressants, tranquilizers, and as intermediates therefor, to methods of preparing the same, to methods of treatment with pharmaceutically effective amounts thereof, and to pharmaceutical compositions containing such compounds as essential active ingredients.

To the best of our knowledge, the compounds of this invention have not heretofore been described or suggested. Substituted 1,3-dihydrospiro[isobenzofuran]s of the formula

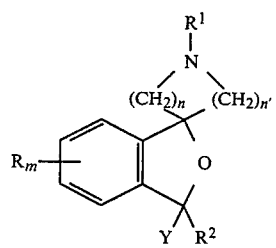

in which R is hydrogen, alkyl, alkoxy, trifluoromethyl, halogen, hydroxy or methylenedioxy; $R^1$ is hydrogen, alkyl, cycloalkylalkyl, alkenyl, phenylalkyl, diphenylalkyl, diphenylmethoxyalkyl, alkanoyl, phenylalkanoyl, benzoyl, benzoylalkyl, phenylhydroxyalkyl, alkoxycarbonyl, phenyloxycarbonyl or cycloalkylcarbonyl; $R^2$ is alkyl or phenyl; Y is hydrogen, alkyl, alkoxy, hydroxy, m, n and n' are integers from 1 to 3; as well as the optical antipodes and pharmaceutically acceptable acid addition salts thereof, are described by Victor J. Bauer et al. in U.S. Pat. No. 3,959,475 granted May 25, 1976. Similarly, Marxer et al. in "Spiro Piperidines. I. Synthesis of Spiro[isobenzofuran-1(3H),4'-piperidines] and Spiro[isobenzofuran-1(3H),3'-piperidines], "J. Org. Chem. Vol. 40, No. 10 (1975), describes various isobenzofurans depicted by the formulae:

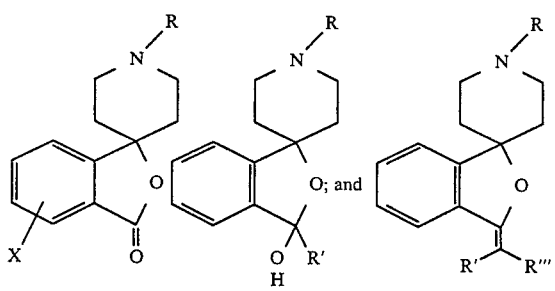

in which X is hydrogen, halogen or methoxy, R is methyl or benzyl, R' is phenyl, substituted phenyl, alkyl, phenylalkyl, diphenylalkyl or thienyl and R'' is alkyl, phenyl, benzyl, 3-methyl-5-isoxazolyl or pyridyl.

However, in this article no pharmaceutical activity is described for the disclosed isobenzofurans.

Neither of these two references describes or suggests the instantly claimed compounds. Each discloses isobenzofurans, not benzo(c)thiophenes. Also, the compounds of this invention cannot be prepared by the syntheses described in the above-mentioned prior art.

This invention relates to novel substituted 1,3-dihydrospiro[benzo(c)thiophene]s of the formula:

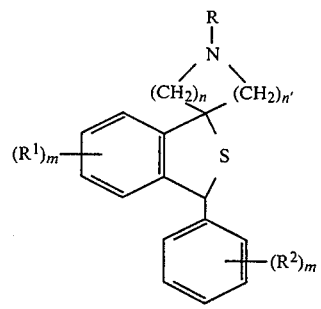

and to the optical antipodes and pharmaceutically acceptable salts thereof, in which R is hydrogen, hydroxy, benzoyloxy, loweralkyl, cycloalkylloweralkyl or cycloalkylloweralkanoyl in which the cycloalkyl portion contains from 3 to 6 carbon atoms, loweralkenyl, phenylalkyl, diphenylalkyl, diphenylmethoxyalkyl, phenoxyalkyl, loweralkanoyl, phenylalkanoyl, benzoyl, benzoylalkyl of the formula $(CH_2)_mCOPhR^1R^2$, phenylhydroxyalkyl, alkyloxycarbonyl of 2 to 6 carbon atoms, phenyloxycarbonyl, cycloalkylcarbonyl of 4 to 8 carbon atoms or

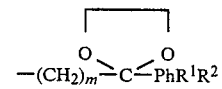

in which Ph is phenyl; $R^1$ and $R^2$ are the same or different and each can be hydrogen, loweralkyl, loweralkoxy, trifluoromethyl, halogen, hydroxy, methylenedioxy or loweralkylthio m, n and n' are integers from 1 to 3; and the sum of n and n' is 3 or 4. In the above, the modifier "lower" means up to 6 carbon atoms.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

Some compounds within the scope of this invention have greater pharmaceutical activity than others. The latter compounds are nevertheless desirable and useful as intermediates in the preparation of the more active compounds. Preferred compounds are those in which R is hydrogen, alkyl of 1 to 3 carbon atoms, especially methyl, or substituted benzoylpropyl with optimum compounds being further limited in that the n and n' are both 2.

The compounds of the invention may be prepared by any of several methods of preparation described below. In this description, R, $R^1$, $R^2$, n, n' and m are, with the exceptions noted as defined previously.

METHOD A

A 2-bromofluorobenzene (I) wherein $R^1$ is not hydroxy, is converted to its lithio derivative (II) by any convenient method, e.g., by reaction with a loweralkyllithium at a temperature from $-100°$ to $-50°$ C. in a solvent such as ether, hexane or tetrahydrofuran. A preferred method involves reaction with butyllithium in tetrahydrofuran at a temperature between $-70°$ and $-60°$ C.

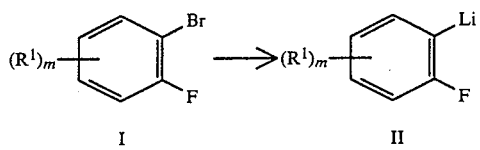

The resulting 2-lithio derivative is reacted with a cycloazalkanone of the formula

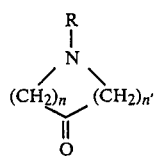

wherein R is alkyl or phenylalkyl under reaction conditions which are commonly used for this type of reaction, e.g., at a temperature of $-80°$ to $-20°$ C., preferably $-80°$ to $-40°$ C., in a solvent such as ether, tetrahydrofuran or hexane to provide a phenylcycloazalkanol (III).

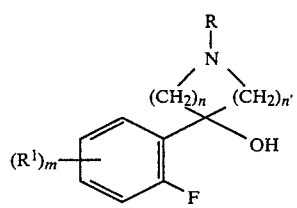

The phenylcycloazalkanol (III) is treated with a benzylmercaptan of the formula

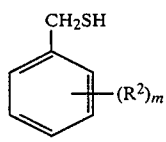

and a Lewis Acid such as titanium tetrachloride or boron trifluoride etherate at a temperature of from ambient to $100°$ C. to provide the corresponding benzylthiophenylcycloazalkane (IV).

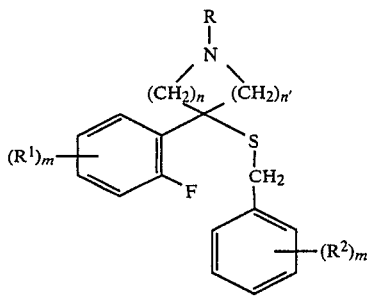

The benzylthiophenylcycloazalkane is cyclized to provide the corresponding 1,3-dihydrospiro[benzo(c)-thiophene-cycloazalkane] (V), a compound of the invention

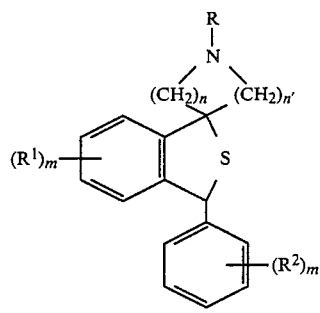

A preferred method includes the use of sodium hydride as a condensing/cyclization agent with a solvent such as dimethylsulfoxide at a temperature of from $25°$ to $100°$ C.

METHOD B

A 1,3-dihydrospiro[benzo(c)thiophene-cycloazalkane] (V) prepared in Method A, is treated with a chloroformate, e.g., an alkyl- or phenyl chloroformate, at a temperature of from $15°$ to $125°$ C., in a solvent such as toluene, benzene or methylene chloride with or without an acid scavenger such as sodium bicarbonate, to provide the corresponding N-alkoxycarbonyl- or N-phenoxycarbonyl-1,3-dihydrospiro[benzo(c)thiophene-cycloazalkane] (VI), a compound of the invention, in which $R^3$ is lower alkyl or phenyl.

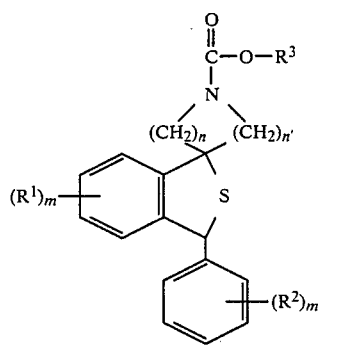

METHOD C

A compound of the invention prepared in Method B is treated with a base such as sodium or potassium hydroxide in a solvent such as water, ethanol or ethylene glycol at a temperature of from 15° C. to the reflux temperature of the reaction mixture or with an acid such as hydrogen bromide in acetic acid at a temperature of from 15° to 125° C. to provide the corresponding N-unsubstituted-1,3-dihydrospiro[benzo(c)thiophene-cycloazalkane], (VII), a compound of the invention.

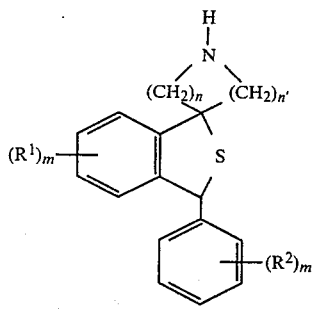

VII

METHOD D

A compound of the invention prepared in Method C can be treated with a compound of the formula

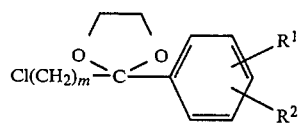

in which $R^1$ is as defined initially, under normal reaction conditions to provide the corresponding compound of the invention, (VIII).

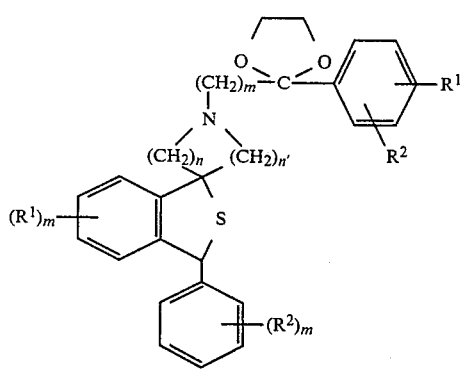

VIII

A preferred method includes the use of potassium iodide as a reaction initiator, sodium bicarbonate as an acid scavenger and dimethylformamide as a solvent at a reaction temperature of about 75° C.

METHOD E

The compound prepared in Method D is subjected to hydrolysis to provide the corresponding compound of the invention in which R is

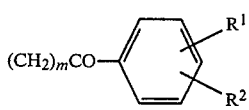

wherein m and $R^1, R^2$ are as defined initially. A preferred method involves the use of a strong acid such as 3N HCl in a solvent such as water or ethanol.

METHOD F

An N-unsubstituted-1,3-dihydrospiro[benzo(c)thiophene-cycloazalkane] (VII) prepared in Method C can be reacted in a known manner with an alkanoyl chloride or anhydride, benzoyl chloride or anhyride, aralkanoyl chloride, alkyl halide, alkenyl halide, cycloalkanoyl halide or aralkyl halide to provide the corresponding compound of the invention in which R is alkanoyl, benzoyl, phenylalkanoyl, alkyl, alkenyl, cycloalkylcarbonyl, phenylalkyl or cycloalkylalkyl.

METHOD G

A compound prepared in Method B, E or F in which R is alkoxycarbonyl, phenoxycarbonyl, alkanoyl, benzoyl, phenylalkanoy cycloalkylcarbonyl or benzoylalkyl can be reduced in a known manner with a reagent such a lithium aluminum hydride or diborane to the corresponding compound if the invention in which R is alkyl, cycloalkyl, phenylalkyl or phenylhydroxyalkyl.

METHOD H

A compound of the invention prepared in Method C can be treated with a peroxide of the formula

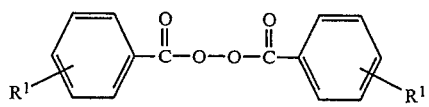

in which $R^1$ is as defined initially, under normal reaction conditions to provide the coresponding compound of the invention (I)

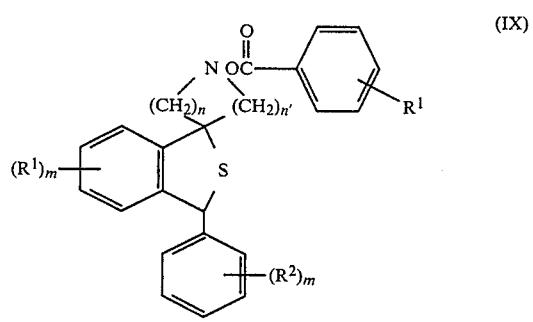

(IX)

A preferred method includes the use of sodium carbonate, benzene solvent and a temperature of about 65°–70° C.

METHOD I

A compound of the invention prepared in Method H can be treated with a base, such as NaOH, under normal hydrolyzing conditions, to provide the corresponding compound of the invention (X).

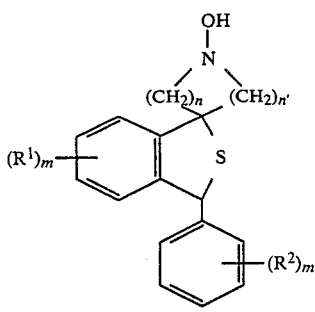

METHOD J

A compound of the invention prepared in Method A, B, C, E, F, G, H or I which contains an alkoxy group on a phenyl ring can be heated with an acid, such as hydrobromic acid or aluminum tribromide, under the normal conditions of hydrolyzing reactions to provide the corresponding hydroxy (phenolic) compound, a compound of the present invention.

The compounds of the present invention ae useful in the treatment of depression in mammals, as demonstrated by their ability to inhibit tetrabenazine-induced depression in mice [International Journal of Neuropharmacology, 8, 73 (1969)], a standard assay for useful antidepressant properties. Thus, at intraperitoneal doses of 1.1 and 2.5 mg/kgs, respectively, 1,3-dihydro-3-phenylspiro[benzo(c)thiophene-1,4'-piperidine] and 1,3-dihydro-1'-methyl-3-phenylspiro[benzo(c)thiophene-1,4'-piperidine] effect a 50% inhibition of the ptosis of tetrabenazine-induced depression in mice. These data illustrate that the compounds are useful as antidepressants in mammals when administered in amounts ranging from 0.1 to 50 mg/kg of body weight per day.

Compounds of the present invention are further useful as tranquilizers due to their depressant action on the central nervous system of mammals. This ability is demonstrated in the Sidman Avoidance Paradigm [Science, 118, 157-8 (1953)], a standard assay for tranquilizers, according to which compounds of the present invention are shown useful as tranquilizers when administered in amounts ranging from 0.1 to about 50 mg/kg per day.

The spiro[benzo(c)thiophene-piperidine]s of the present invention generally exhibit minimal or are devoid of anticholinergic activity as demonstrated by their ability to protect mice against the lethal effects of physostigmine in a standard assay such as the one described in Example 68.

Other compounds of the invention include:

1,3-dihydro-1'-ethoxycarbonyl-3-phenylspiro[benzo(c)thiophene-1,4'-piperidine];

1,3-dihydro-1'-[(3-hydroxy-3-phenyl)propyl]-3-phenylspiro[benzo(c)thiophene-1,4'-piperidine];

1'-[4-(4-fluorophenyl)-4-hydroxybutyl]-1,3-dihydro-3-phenylspiro[benzo(c)thiophene-1,4'-piperidine];

1'-cyclohexylmethyl-1,3-dihydro-3-phenylspiro[benzo(c)thiophene-1,4'-piperidine];

1,3-dihydro-1'-diphenylmethoxyethyl-3-phenyl-spiro[benzo(c)thiophene-1,4'-piperidine);

1'-allyl-1,3-dihydro-3-phenylspiro[benzo(c)thiophene-1,4'-piperidine];

1,3-dihydro-1'-methyl-3-(4-methoxyphenyl)spiro[benzo(c)thiophene-1,4'-piperidine];

6-fluoro-3-(4-fluorophenyl)-1,3-dihydro-1'-methylspiro[benzo(c)thiophene-1,4'-piperidine];

1,3-dihydro-3-(4-methoxyphenyl)spiro[benzo(c)thiophene-1,4'-piperidine];

1'-[3-(4-fluorobenzoyl)propyl]-1,3-dihydro-3-(4-methoxyphenyl)spiro[benzo(c)thiophene-1,4'-piperidine];

6-fluoro-1'-[3-(4-fluorobenzoyl)propyl]-1,3-dihydro-3-phenylspiro[benzo(c)thiophene-1,4'-piperidine];

4,6-difluoro-1,3-dihydro-3-phenylspiro[benzo(c)thiophene-1,4'-piperidine];

6-fluoro-1'-[3-(4-fluorobenzoyl)propyl]-3-(4-fluorophenyl)-1,3-dihydro-spiro[benzo(c)thiophene-1,4'-piperidine];

1,3-dihydro-1'-(4,4-diphenylbutyl)-3-(4-trifluoromethylphenyl)-spiro[benzo(c)thiophene-1,4'-piperidine];

3-(3-bromophenyl)-1,3-dihydro-1'-(3-phenoxypropyl)spiro[benzo(c)thiophene-1,4'-piperidine];

1'-benzoyl-1,3-dihydro-3-(4-hydroxyphenyl)spiro[benzo(c)thiophene-1,4'-piperidine];

1,3-dihydro-3-phenyl-1'-phenylacetylspiro[benzo(c)thiophene-1,4'-piperidine];

1,3-dihydro-3-(3,4-methylenedioxyphenyl)-1'-methylspiro[benzo(c)thiophene-1,4'-piperidine];

1,3-dihydro-1'-hydroxy-3-(4-methoxyphenyl)spiro[benzo(c)thiophene-1,4'-piperidine];

3-(3,4-dichlorophenyl)-1,3-dihydro-1'-methylspiro[benzo(c)thiophene-1,3'-pyrrolidine];

1,3-dihydro-1'-methyl-3-(2-methylthiophenyl)spiro[benzo(c)thiophene-1,4'-piperidine];

1,3-dihydro-1'-methyl-6-methyltho-3-phenylspiro[benzo(c)thiophene-1,3'-pyrrolidine];

1'-cyclopropylacetyl-1,3-dihydro-3-phenylspiro[benzo(c)thiophene-1,4'-piperidine];

6-methyl-1,3-dihydro-1'-methyl-3-phenylspiro[benzo(c)thiophene-1,4'-piperidine];

7-methoxy-1,3-dihydro-1'-methyl-3-phenylspiro[benzo(c)thiophene-1,4'-piperidine];

5-trifluoromethyl-1,3-dihydro-1'-methyl-3-phenylspiro[benzo(c)thiophene-1,4'-piperidine];

4-hydroxy-1,3-dihydro-1'-methyl-3-phenylspiro[benzo(c)thiophene-1,4'-piperidine];

5,6-methylenedioxy-1,3-dihydro-1'-methyl-3-phenylspiro[benzo(c)thiophene-1,4'-piperidine];

1,3-dihydro-1'-methyl-3-(2-methoxyphenyl)spiro[benzo(c)thiophene-1,4'-piperidine];

1'-benzoylpropyl-1,3-dihydro-3-phenylspiro[benzo(c)thiophene-1,4'-piperidine];

1'-benzoylpropyl-1,3-dihydro-3-phenylspiro[benzo(c)thiophene-1,4'-piperidine]ethylene ketal;

1'-(4-fluorophenethyl)-1,3-dihydro-3-phenylspiro[benzo(c)thiophene-1,4'-piperidine]; and 1,3-dihydro-1'-(3,4-dimethoxyphenyl)propyl-3-phenylspiro[benzo(c)thiophene-1,4'-piperidine].

Effective quantities of the compounds of the invention may be administered to a patient by any one of various mehods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as microcrystalline cellulose, gum tragacanth or gelatin; and excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain a pharmaceutically effective amount, i.e., at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampuls, disposable syringes or multiple dose vials made of glass or plastic.

The invention is further illustrated by the following examples.

EXAMPLE 1 a. 46 ml of 2.4M n-butyllithium are added over a 15 minute span to a mixture cooled to −70° C. of 17.5 g of 2-bromofluorobenzene and 50 ml of tetrahydrofuran. After total addition, the reaction mixture is stirred at between −60° to −70° C. for 15 minutes to enable complete lithiation, which results in a tan colored solution. A mixture of 11.3 g of 1-methyl-4-piperidone in 20 ml of tetrahydrofuran is added to the solution at a rate to maintain the reaction medium's temperature below −60° C. After total addition, the reaction mixture is stirred at the same low temperature for one hour before being permitted to warm to ambient temperature. Water is added and the biphasic mixture is permitted to separate into its organic and aqueous phases. The organic phase is collected and the aqueous phase is extracted thrice with ether and the ether extracts are combined with the organic phase. The combined organic solution is extracted with an excess of 2N hydrochloric acid and then discarded. The acidic solution is basified with ammonium hydroxide, producing a heavy oil which is dissolved in a 1:1 ethyl acetate ether mixture. This solution is dried and then concentrated to dryness, leaving a viscous oil which crystallizes with cooling. The solid product is recrystallized from a benzene-hexane mixture to give prisms, mp 127°-129° C. of 4-(2-fluorophenyl)-4-hydroxy-1-methylpiperidine.

b. A reaction mixture of 4.5 g of 4-(2-fluorophenyl)-4-hydroxy-1-methylpiperidine, 8 ml of benzyl mercaptan, 10 ml of boron trifluoride etherate and 10 ml of glacial acetic acid is stirred at 65° C. for 16 hours. The excess reagents are removed at 70° C. in vacuo and the residue is taken up with a 1:1 ether-2N hydrochloric acid mixture and then permitted to stand at a lowered temperature for two hours. The cooled mixture is filtered to collect its crystalline product. The product is recrystallized from an acetone-ether mixture to give colorless prisms, mp 182°-184° C. of 4-benzylthio-4-(2-fluorophenyl)1-methylpiperidine hydrochloride.

c. A mixture of 0.9 g of 50% sodium hydride in 20 ml of dimethylsulfoxide is heated at 80°-85° C. in a nitrogen atmosphere for 30 minutes to produce a solution of sodium methylsulfinylmethide. This solution is permitted to cool to ambient temperature. A solution of 4.9 g of 4-benzylthio-4-(2-fluorophenyl)-1-methylpiperidine, free base of b, in 10 ml of dimethylsulfoxide is added over a 5 minute span. After total addition, the mixture is stirred at ambient temperature for one hour and then poured onto ice-water. The resulting solid, collected by filtration, is recrystallized from an ether-hexane mixture to give colorless prisms, mp 120°-121° C., of 1,3-dihydro-1'-methyl-3-phenylspiro[benzo(c)thiophene-1,4'-piperidine].

Analysis: Calculated for $C_{19}H_{21}NS$: 77.24%C; 7.17%H; 4.74%N; 10.85%S. Found: 77.31%C; 7.20%H; 4.59%N; 10.71%S.

d. With the substitution of 1-methyl-3-pyrrolidone for 1-methyl-4-piperidone into the manipulative procedure of Method A, 3-(2-fluorophenyl)-3-hydroxy-1-methylpyrrolidine may be obtained.

e. Starting with 3-(2-fluorophenyl(-3-hydroxy-1-methylpyrrolidine, the manipulative procedures of Method A may be implemented to provide 1,3-dihydro-1'-methyl-3-phenylspiro[benzo(c)thiophene-1,3'-pyrrolidine].

f. The substitution of 1-benzyl-3-pyrrolidone for 1-methyl-3-pyrrolidone into the manipulative procedures of Example 1d and 1e may provide 1'-benzyl-1,3-dihydro-3-phenylspiro[benzo(c)thiophene-1,3'-pyrrolidine].

g. With the substitution of 1-methyl-3-piperidone for 1-methyl-4-piperidone into the manipulative procedure of Example 1a, 3-(2-fluorophenyl)-3-hydroxy-1-methylpiperidine may be obtained.

h. Starting with 3-(2-fluorophenyl)-3-hydroxy-1-methylpiperidine, the manipulative procedures of Example 1b and 1c may be implemented to provide 1,3-dihydro-1'-methyl-3-phenylspiro[benzo(c)thiophene-1,3'-piperidine].

EXAMPLE 2 a. 9.9 ml (11.9 g) of 4-chlorobenzyl mercaptan and 11.1 ml of boron trifluoride etherate are added sequentially to 5.00 g of 4-(2-fluorophenyl)-4-hydroxy-1-methylpiperidine. Example 1a, in 11.1 ml of glacial acetic acid. The reaction is stirred at 55°-60° C. for 48 hours. The excess reagents are removed at 80° C. in vacuo and the residue is taken up with a 1:1 ether-2N hydrochloride acid mixture. This biphasic mixture is stirred for 2.5 hours and then for an additional ten minutes after 50 ml of ice are added. The ether layer is decanted off. The aqueous layer is sequentially washed with ether and filtered to collect a crude product. The product is washed with a small portion of water and then a large portion of ether to give a white powder. The powder is recrystallized from acetone to give white crystals, mp 164°-166° C. of 4-(4-chlorobenzylthio)-4-(2-fluorophenyl)-1-methylpiperidine hydrochloride.

Analysis: Calculated for $C_{19}H_{21}NClFS.HCl$: 59.08%C; 5.74%H; 3.63%N; 4.92%F. Found: 59.04%C; 5.56%H; 3.68%N; 4.78%F.

b. A solution of sodium methylsulfinylmethide is produced from 0.7 g of (50%) sodium hydride and 15 ml of dimethylsulfoxide as in Example 1c. A solution of 4.2 g of 4-(4-chlorobenzylthio)-4-(2-fluorophenyl)-1-methylpiperidine, free base of a, in 15 ml of dimethylsulfoxide is added to this solution over a three minute span. After total addition, the mixture is stirred at ambient temperature for one hour and then poured onto 70 ml of ice-water. The mixture is diluted with water to 120 ml total volume before being filtered to collect the crude product. The product is washed with water and then dissolved with ether. The ethereal solution is sequentially washed thrice with water and once with a saturated sodium chloride solution and dried to give yellow-white crystals. The crystals are chromatographed with ether through an alumina column to give white crystals, mp 121°-123° C. of 3-(4-chlorophenyl)-1,3-dihydro-1'-methylspiro[benzo(c)thiophene-1,4'-piperidine].

Analysis: Calculated for $C_{19}H_{20}ClNS$: 69.19%C; 6.11%H; 4.25%N; 10.75%Cl. Found: 69.24%C; 6.21%H; 3.96%N; 10.74%Cl.

EXAMPLE 3

A mixture of 2.3 g of 1,3-dihydro-1'-methyl-3-phenylspiro[benzo(c)thiophene-1,4'-piperidine], Example 1, 1.4 g of phenyl chloroformate and 0.5 g of sodium bicarbonate in 40 ml of methylene chloride is stirred at ambient temperature for 4 hours before being filtered. The filtrate is sequentially washed with a dilute sodium hydroxide solution and water and dried. The solvent is removed in vacuo, leaving a solid residue which is recrystallized from a benzene-hexane mixture to give rosettes, mp 171°-173° C., of 1,3-dihydro-1'-phenoxycarbenyl-3-phenylspiro[benzo(c)thiophene-1,4'-piperidine].

Analysis: Calculated for $C_{25}H_{23}NO_2S$: 74.78%C; 5.77%H; 3.49%N. Found: 75.04%C; 5.84%H; 3.43%N.

EXAMPLE 4 a. A mixture of 3.0 g of 1,3-dihydro-1'-phenoxycarbonyl-3-phenylspiro[benzo(c)thiophene-1,4'-piperidine], Example 3, 8.0 g of potassium hydroxide pellets in 50 ml of ethylene glycol is stirred at 155° C. until a clear solution results. The solution is permitted to cool, diluted with water and the biphasic mixture extracted thrice with chloroform. The combined chloroform extracts are washed carefully with water and dried and the chloroform removed leaving a solid residue. The residue is recrystallized from an acetone-hexane to give prisms, mp 142°-144° C. of 1,3-dihydro-3-phenylspiro[benzo(c)thiophene-1,4'-piperidine].

Analysis: Calculated for $C_{18}H_{19}NS$: 76.83%C; 6.80%H; 4.98%N; 11.39%S. Found: 77.05%C; 6.84%H; 4.68%N; 11.26%S.

EXAMPLE 5

A mixture of 2.8 g of 1,3-dihydro-3-phenylspiro[benzo(c)thiophene], Example 4a, 1.4 g of benzyl chloride and 3.5 g of sodium bicarbonate in 50 ml of dimethylformamide is stirred at 70° C. for two hours Water is added to the cooled mixture and the biphasic mixture is extracted four times with methylene chloride. The methylene chloride extracts are dried and concentrated in vacuo leaving an oily residue which crystallizes in standing. The product is recrystallized from an ether-hexane mixture to give fine needles, mp 144°-145° C. of 1'-benzyl-1,3-dihydro-3-phenylspiro[benzo(c)thiophene-1,4'-piperidine].

Analysis: Calculated for $C_{25}H_{25}NS$: 80.82%C; 6.78%H; 3.78%N; 8.63%S. Found: 80.81%C; 6.68%H; 3.66%N; 8.76%S.

EXAMPLE 6

A mixture of 3.9 g of 1,3-dihydro-3-phenylspiro[benzo(c)thiophene-1,4'-piperidine], Example 4, 3.4 g of dibenzoyl peroxide, 4.0 g of potassium carbonate in 60 ml of benzene is stirred at a temperature of 65°-70° C. for 16 hours before being filtered. The filtrate is washed and dried and the solvent removed in vacuo, leaving a crude oily product. The product is chromatographed through a silica gel column with a methylene chloride eluant to provide 1'-benzoyloxy-1,3-dihydro-3-phenylspiro[benzo(c)thiophene-1,4'-piperidine].

Analysis: Calculated for $C_{25}H_{23}NO_2S$: 74.78%C; 5.77%H; 3.48%N. Found: 74.67%C; 5.82%H; 3.33%N.

EXAMPLE 7

A mixture of 0.6 g of 1,3-dihydro-3-phenylspiro[benzo(c)thiophene-1,4'-piperidine], Example 4, 0.7 g of γ-chloro-4-fluorobutyrophenone ethylene ketal, 0.5 g of potassium iodide and 0.5 g of sodium bicarbonate in 15 ml of dimethylformamide is stirred at 80° C. for 16 hours. The reaction mixture is permitted to cool and then diluted with methylene chloride. The diluted mixture is filtered and the filtrate concentrated in vacuo leaving an oil which crystallizes with cooling. The solid product is recystallized from an ether-pentane mixture to give tannish crystals, mp 121°-122° C. of 1'-[3-(4-fluorobenzoyl)propyl]-1,3-dihydro-3-phenylspiro[benzo(c)thiophene-1,4'-piperidine]ethylene ketal.

Analysis: Calculated for $C_{30}H_{32}FNO_2S$: 73.59%C; 6.59%H; 2.86%N. Found: 73.81%C; 6.33%H; 2.74%N.

EXAMPLE 8

A sample of the oil, 1'-[3-(4-fluorobenzoyl)propyl]-1,3-dihydro-3-phenylspiro[benzo(c)thiophene-1,4'-piperidine]ethylene ketal, oil of Example 7, is stirred with an excess of 3N hydrochloric acid in ethanol for 16 hours. The excess acid and ethanol are removed in vacuo and the residue taken up with a mixture of 20% sodium hydroxide and a methylene chloride mixture. The biphasic mixture is permitted to separate and the organic phase is collected and dried and the solvent removed leaving a reddish oil which crystallizes with cooling. The solid product is recrystallized from an ether-pentane mixture to give crystals, mp 118°–120° C., of 1'-[3-(4-fluorobenzoyl)propyl]-1,3-dihydro-3-phenylspiro[benzo(c)thiophene-1,4'-piperidine].

Analysis: Calculated for $C_{28}H_{28}FNOS$: 75.47%C; 6.33%H; 3.14%N; 7.20%S. Found: 75.74%C; 6.45%H; 2.93%N; 7.21%S.

EXAMPLE 9

A sample of 3-(4-chlorophenyl)-1,3-dihydro-1'-methylspiro[benzo(c)thiophene-1,4'-piperidine], Example 2, is treated according to the procedure of Example 3, to obtain 3-(4-chlorophenyl)-1,3-dihydro-1'-phenoxycarbonylspiro[benzo(c)thiophene-1,4'-piperidine], as a glassy solid. This solid is chromatographed through a silica gel column with an eluant of methylene chloride to obtain a pure white solid product, mp 211°–212° C.

Analysis: Calculated for $C_{25}H_{22}ClNO_2S$: 68.81%C; 5.08%H; 3.21%N. Found: 69.04%C; 5.03%H; 2.97%N.

EXAMPLE 10

A cold stirred solution of 1,3-dihydro-3-phenylspiro[benzo(c)thiophene-1,4'-piperidine], Example 4, and triethylamine in 50 ml of chloroform is treated dropwise with a solution of acetyl chloride in chloroform to provide 1'-acetyl-1,3-dihydro-3-phenylspiro[benzo(c)thiophene-1,4'-piperidine].

EXAMPLE 11

A solution of 1'-acetyl-1,3-dihydro-3-phenylspiro[benzo(c)thiophene-1,4'-piperidine], Example 10, in tetrahydrofuran is treated carefully with a stirred suspension of lithium aluminum hydride in tetrahydrofuran to provide 1'-ethyl-1,3-dihydro-3-phenylspiro[benzo(c)thiophene-1,4'-piperidine].

EXAMPLE 12 a. 13.3 ml of boron trifluoride etherate are added to a well stirred solution of 6.0 g of 4-(2-fluorophenyl)-4-hydroxy-1-methylpiperidine, Example 1a, and 9 ml of 4-methylbenzyl mercaptan in 13.3 ml of glacial acetic acid. After this addition the reaction mixture is heated at 60°–65° C. for two hours. Thereafter any excess reagents are removed in vacuo at 70° C., leaving a residue which is stirred with 50 ml of 2N hydrochloric acid and 50 ml of ether producing a semisolid product in a resultant intermediate layer. This semisolid is collected and converted to its free base with a 20% sodium hydroxide solution. The free base is converted to a hydrobromide which is recrystallized from a methanol-ether mixture, leaving a white solid, mp 182°–184° C., of 4-(2-fluorophenyl-1-methyl-4-(4-methylbenzylthio)piperidine hydrobromide.

b. A solution of 0.7 g sodium hydride in 50% mineral oil in 20 ml of dimethylsulfoxide is added over a five minute span to a mixture of 4.1 g of 4-(2-fluorophenyl)-1-methyl-4-(4-methylbenzylthio)piperidine, free base of a, in 15 ml of dimethylsulfoxide. After total addition, the reaction mixture is stirred for 30 minutes before being poured into 100 ml of ice-water. The biphasic mixture is filtered collecting a tan solid which is dissolved in dichloromethane and then column chromatographed on an alumina/ether column with an ether eluant. The chromatographed product is recrystallized from an ether-hexane mixture to provide the product, mp 121°–122° C., of 1,3-dihydro-1'-methyl-3-(4-methylphenyl)spiro[benzo(c)thiophene-1,4'-piperidine].

Analysis: Calculated for $C_{20}H_{23}NS$: 77.62%C; 7.49%H; 4.53%N. Found: 77.63%C; 7.67%H; 4.35%N.

EXAMPLE 13

A solution of 1.0 g of 1,3-dihydro-1'-methyl-3-(4-methylphenyl)spiro[benzo(c)thiophene-1,4'-piperidine], Example 12 in 10 ml of dichloromethane is added to a stirring slurry of 0.6 g of phenyl chloroformate and 0.2 g of sodium bicarbonate in 20 ml of dichloromethane. After addition, the mixture is permitted to stir at ambient temperature for 24 hours before being successively filtered, diluted with 50 ml of methylene chloride, extracted with a 10% sodium hydroxide solution, extracted with water, dried and filtered. The solvent is removed, leaving an oil. The oil is column chromatographed on a silica gel/methylene chloride column with a methylene chloride eluant to obtain a white fluffy solid which is recrystallized from a benzene-hexane mixture to obtain the product, mp 179°–180° C., of 1,3-dihydro-3-(4-methylphenyl)-1'-phenoxycarbonylspiro[benzo(c)thiophene-1,4'-piperidine].

Analysis: Calculated for $C_{26}H_{25}NO_2S$: 75.15%C; 6.06%H; 3.37%N. Found: 75.24%C; 6.10%H; 3.16%N.

EXAMPLE 14

A mixture of 0.5 g of 1,3-dihydro-3-phenylspiro[benzo(c)thiophene-1,4'-piperidine], Example 4, 0.4 g of cyclopropylcarbonyl chloride and 1.0 g of sodium bicarbonate in 20 ml of dichloromethane is stirred at ambient temperature for 16 hours. The well stirred mixture is filtered and the filtrate is concentrated to dryness. The residue is passed through a silica gel/ether column with an ether eluant to provide pure 1'-cyclopropylcarbonyl-1,3-dihydro-3-phenylspiro[benzo(c)thiophene-1,4'-piperidine].

Analysis: Calculated for $C_{22}H_{23}NOS$: 75.60%C; 6.63%H; 4.01%N. Found: 75.56%C; 6.69%H; 3.71%N.

EXAMPLE 15

A mixture of 14.4 g of 3-(4-chlorophenyl)-1,3-dihydro-1'-phenoxycarbonylspiro[benzo(c)thiophene-1,4'-piperidine], Example 9, 220 ml of ethylene glycol and 35.3 g of potassium hydroxide pellets is treated according to the manipulative procedure of Example 4, above, to provide a yellow-tinted white crystalline solid. This solid is swirled with pentane and then permitted to stand at 0° C. for 16 hours before the mixture is filtered to provide a white powder which is recrystallized from an acetone-hexane mixture to provide the product, mp 138°–140° C., of 3-(4-chlorophenyl)-1,3-dihydrospiro[benzo(c)thiophene-1,4'-piperidine].

Analysis: Calculated for $C_{18}H_{18}ClNS$: 68.46%C; 5.75%H; 4.44%N; 11.23%Cl. Found: 68.48%C; 5.81%H; 4.34%N; 11.27%Cl.

EXAMPLE 16

1.4 g of sodium bicarbonate and 1.4 g of potassium iodide are added to a mixture of 2.0 g of 3-(4-chlorophenyl)-1,3-dihydrospiro[benzo(c)thiophene-1,4'-piperidine], Example 15 and 2.0 g of γ-chloro-4-fluorobutyrophenone ethylene ketal in 20 ml of dimethylformamide. The reaction mixture is heated with stirring at 80°–85° C. for 17 hours. The mixture is permitted to cool to ambient temperature before being diluted with 50 ml of chloroform. The diluted solution is concentrated to dryness and the residue partitioned between 100 ml of methylene chloride and 50 ml of water. The two layers are shaken and then permitted to separate. The organic layer is washed sequentially with water and a saturated sodium chloride solution and dried effecting an oil. The oil is column chromatographed on an alumina column with ether to provide the clear oil of 3-(4-chlorophenyl)-1'-[3-(4-fluorobenzoyl)propyl]-1,3-dihydrospiro[benzo(c)thiophene-1,4'-piperidine]ethylene ketal.

Analysis: Calculated for $C_{30}H_{31}ClFNO_2S$: 68.76%C; 5.96%H; 2.6%N. Found: 68.63%C; 5.89%H; 2.71%N.

EXAMPLE 17

A mixture of 2.0 g of 3-(4-chlorophenyl)-1,3-dihydrospiro[benzo(c)thiophene-1,4'-piperidine], Example 15, 0.7 g of chloromethylcyclopropane, 1.4 g of potassium iodide and 1.4 g of sodium bicarbonate in 20 ml of dimethylformamide is heated with stirring at 80°–85° C. for 17 hours. The reaction mixture is permitted to cool to ambient temperature before being diluted with 75 ml of water and 30 ml of methylene chloride. The aqueous phase is extracted twice with methylene chloride and all the methylene chloride solutions are combined. The combined solutions are washed, sequentially, with water and saturated sodium chloride solution and then dried effecting a clear oil. The oil is chromatographed on an alumina column with an ether eluant to obtain the oil with enhanced purity. This oil is converted to its maleic acid salt which is recrystallized from an acetone-ether mixture to obtain the salt, mp 217.5°–218° C. of 3-(4-chlorophenyl)-1'-cyclopropylmethyl-1,3-dihydrospiro[benzo(c)thiophene-1,4'-piperidine]maleate.

Analysis: Calculated for $C_{22}H_{24}ClNS \cdot C_4H_4O_4$: 64.25%C; 5.81%H; 2.88%N; 7.30%Cl Found: 64.13%C; 5.82%H; 2.77%N; 7.36%Cl.

EXAMPLE 18

A reaction mixture of 4.2 g of 3-(4-chlorophenyl)-1'-[3-(4-fluorobenzoyl)propyl]-1,3-dihydrospiro[benzo(c)thiophene-1,4'-piperidine]ethylene ketal, crude oil of Example 16, and 22 ml of 3N hydrochloric acid in 60 ml of ethanol is stirred at ambient temperature for 20 hours and then cooled to 0° C. for an additional 20 hours. Any gummy precipitate is removed by filtration and the filtrate is subjected to rotary evaporation at 50° C. leaving an orange residue. The residue is equilibrated with 50 ml of 20% sodium hydroxide and 100 ml of a 1:1 mixture of ether and methylene chloride. The layers are separated and the aqueous layer is extracted with an additional 40 ml of the aforesaid ether, methylene chloride mixture. The organic portions are combined and these combined portions are diluted with 50 ml of ether and then sequentially washed with water and saturated sodium chloride, dried and evaporated leaving a clear orange oil. The oil is chromatographed on a silica gel column with an eluant of 5% methanol in methylene chloride mixture, providing a purified oil. The oil is dissolved in ether and converted to its hydrobromide salt, a white powder. The powder is recrystallized twice from a methanol-ether mixture to provide the salt, mp 240°–241° C., of 3-(4-chlorophenyl)-1'-[3-(4-fluorobenzoyl)propyl]-1,3-dihydrospiro[benzo(c)thiophene-1,4'-piperidine]hydrobromide.

Analysis: Calculated for $C_{18}H_{22}ClFNOS \cdot HBr$: 59.96%C; 5.03%H; 2.05%N. Found: 60.03%C; 4.85%H; 2.36%N.

EXAMPLE 19 a. A reaction mixture of 10.0 g of 4-(2-fluorophenyl)-4-hydroxy-1-methylpiperidine, Example 1a, 17.5 ml of 3,4-dichlorobenzyl mercaptan and 22 ml of boron trifluoride etherate in 22 ml of glacial acetic acid is stirred at 60°–65° C. for 16 hours. Thereafter, the solvent is removed under reduced pressure and the residue triturated with a mixture of ether and 1N hydrochloric acid. The mixture is stirred at 0° C. for two hours and then the resulting white crystalline precipitate is collected by filtration. The precipitate is recrystallized from an acetone-ether mixture, leaving colorless needles, mp 188°–190° C., of 4-(3,4-dichlorobenzylthio)-4-(2-fluorophenyl)-1-methylpiperidine hydrochloride.

b. 8.2 g of 4-(3,4-dichlorobenzylthio)-4-(2-fluorophenyl)-1-methylpiperidine, free base of a, in 20 ml of dimethylsulfoxide are carefully added over a 20 minute span to a cooled solution of sodium methylsulfinylmethide prepared by heating 1.2 g of sodium hydride (50%) in 50 ml of dimethylsulfoxide at 80° C. for 30 minutes. After total addition, the reaction mixture is stirred at ambient temperature for 30 minutes and then quenched with water. The biphasic mixture is extracted with methylene chloride and the methylene chloride extract is dried and concentrated, leaving a brownish oil which crystallizes with standing. The product is converted, in ether, to its maleic acid salt which is recrystallized from an acetone-ether mixture to give the salt, mp 212°–213° C., of 3-(3,4-dichlorophenyl)-1,3-dihydro-1'-methylspiro[benzo(c)thiophene-1,4'-piperidine]maleate.

Analysis: Calculated for $C_{19}H_{19}Cl_2NS \cdot C_4H_4O_4$: 57.50%C; 4.83%H; 2.95%N; 14.76%C. Found: 57.75%C; 4.81%H; 2.72%N; 14.49%C.

EXAMPLE 20 a. A sample of 2-bromo-1,4-difluorobenzene is treated according to the multi-step procedure of Example 1a to ultimately obtain 4-(2,5-difluorophenyl)-4-hydroxy-1-methylpiperidine, which is converted to its maleic acid salt which is recrystallized from an acetone-ether mixture to obtain the pure salt, m.p. 163°–165° C.

b. A mixture of 4-(2,5-difluorophenyl)-4-hydroxy-1-methyl-piperidine, free base of a, 4 ml of boron trifluoride etherate, 5 ml of benzyl mercaptan and 5 ml of glacial acetic acid is stirred at 65° C. for 16 hours. Excess acid is removed under reduced pressure with the residue equilibrated with 0.5N hydrochloric acid and ether and the resulting solution is stirred at 10°–20° C. for four hours. The resulting crystalline precipitate is sequentially collected by filtration, basified and extracted with ether providing the desired product as an oil. The oil is converted to its maleic acid salt which is recrystallized from an acetone-ether mixture to provide prisms, m.p. 164°–166° C. of 4-benzylthio-4-(2,5-difluorophenyl)-1-methylpiperidine maleate.

c. A solution of sodium methylsulfinylmethide which was prepared by heating 250 mg of sodium hydride (50% dispersion, washed with pentane) in 10 ml of dimethylsulfoxide at 80° C. for 30 minutes is added over a five-minute span at ambient temperature to a mixture of 4-benzylthio-4-(2,5-difluorophenyl)-1-methylpiperidine, free base of b, in 5 ml of dimethylsulfoxide. After total addition, the mixture is stirred at ambient temperature for 30 minutes before being poured onto 50 g of ice water. The mixture is extracted thrice with methylene chloride and the combined extracts are washed with water and dried. The methylene chloride is removed under vacuum, leaving a solid residue. The residue is recrystallized from an ether-pentane mixture to give granular crystals, m.p. 136°–317° C. of 6-fluoro-1,3-dihydro-1'-methyl-3-phenylspiro[benzo(c)thiophene-1,4'-piperidine].

Analysis: Calculated for $C_{19}H_{20}FNS$: 72.81%C; 6.42%H; 4.47%N; 6.06%F; 10.23%S. Found: 72.52%C; 6.46%H; 4.27%N; 5.88%F; 10.49%S.

EXAMPLE 21

A mixture of 0.3 g of 6-fluoro-1,3-dihydro-1'-methyl-3-phenylspiro[benzo(c)thiophene-1,4'-piperidine] and 0.3 g of phenyl chloroformate in 10 ml of methylene chloride which was previously stirred at ambient temperature for 16 hours is sequentially quenched with water, washed with 10% sodium hydroxide and dried. The reaction mixture is concentrated under vacuum leaving a viscous oil which crystallized with standing. The solid product is recrystallized from an ether-pentane mixture to give prisms, m.p. 156°–158° C. of 6-fluoro-1,3-dihydro-3-phenyl-1'-phenoxycarbonylspiro[benzo(c)thiophene-1,4'-piperidine].

Analysis: Calculated for $C_{25}H_{22}FNO_2S$: 71.57%C; 5.29%H; 3.34%N. Found: 71.65%C; 5.38%H; 3.15%N.

EXAMPLE 22

A solution of 2.5 g of 3-(3,4-dichlorophenyl)-1,3-dihydro-1'-methylspiro[benzo(c)thiophene-1,4'-piperidine], free base of Example 19, and 1.3 g of phenyl chloroformate in 30 ml of methylene chloride is stirred at ambient temperature for 16 hours. The well stirred solution is washed successively with dilute sodium hydroxide and water and then dried, effecting a crystalling product. The product is recrystallized from an acetone-pentane mixture to give fine needles, m.p. 200°–202° C. of 3-(3,4-dichlorophenyl)-1,3-dihydro-1'-phenoxycarbonylspiro[benzo(c)thiophene-1,4'-piperidine].

Analysis: Calculated for $C_{25}H_{21}Cl_2NO_2S$: 63.83%C; 4.50%H; 2.98%N. Found: 63.71%C; 4.56%H; 2.93%N.

EXAMPLE 23 a. 82 ml of boron trifluoride etherate are added to a mixture of 30.0 g of 4-(2-fluorophenyl)-4-hydroxy-1-methylpiperidine of Example 1a and 82 ml of 2-methylbenzyl mercaptan. The resulting solution is stirred and heated at 75° C. for six hours and then the excess reagents are distilled at 80°–100° C. The oil remaining in the flask is stirred with 250 ml of 2N HCl and 500 ml of ether for one hour after which 1500 ml of ice is added to form a slurry. The slurry is stirred an additional hour and filtered to yield a white solid which is washed with ether and air dried. The material is recrystallized from methanol-acetone-ether to give the product, 4-(2-fluorophenyl)-1-methyl-4-(2-methylbenzylthio)piperidine hydrochloride. An elemental analysis sample was further recrystallized from acetone-ether to give a sample with constant melting point of 206°–208° C.

Analysis: Calculated for $C_{20}H_{24}FNS.HCl$: 65.64%C; 6.89%H; 3.83%N. Found: 65.46%C; 6.82%H; 3.55%N.

B. A 0.73 g sample of sodium hydride, 50% in mineral oil, is cleaned by triturating with hexane. To the cleaned sodium hydride, is added 20 ml of dimethylsulfoxide and the solution heated in an oil bath at 80°–90° C. for 30 minutes. The solution is cooled to room temperature and 4.05 g of 4-(2-fluorophenyl)-1-methyl-4-(2-methylbenzylthio)piperidine of Example 23a in 15 ml of dimethylsulfoxide is added over a 5-minute period. The reaction is stirred for thirty minutes, poured into 100 ml of ice-water, and filtered. The resulting tan solid is dissolved in dichloromethane and chromatographed on an $Al_2O_3$/ether column (eluting with ether) m.p. 132°–143° C. The sample is recrystallized from ether-hexane to obtain 1,3-dihydro-1'-methyl-3-(2-methylphenyl)spiro[benzo(c)thiophene-1,4'-piperidine], m.p. 132°–134° C.

Analysis: Calculated for $C_{20}H_{23}NS$: 77.62%C; 7.49%H; 4.53%N. Found: 77.63%C; 7.67%H; 4.35%N.

EXAMPLE 24

A suspension of 3-(3,4-dichlorophenyl)-1,3-dihydro-1'-phenoxycarbonylspiro[benzo(c)thiophene-1,4'-piperidine] (2.35 g), 7.0 g of potassium hydroxide (85%) in 30 ml of ethylene glycol is stirred at 160° C. for 30 minutes. The mixture is cooled, diluted with water and extracted with 3 portions (100 ml) of dichloromethane. Following drying ($MgSO_4$) and evaporation in vacuo, the crude amine is converted to a crystalline maleate in ether. Recrystallization from methanol-ether gives rhombic crystals of 3-(3,4-dichlorophenyl)-1,3-dihydrospiro[benzo(c)thiophene-1,4'-piperidine]maleate m.p. 192°–193° C.

Analysis: Calculated for $C_{18}H_{17}Cl_2NS.C_4H_4O_4$: 56.65%C; 4.54%H; 3.00%N; 15.20%Cl. Found: 56.75%C; 4.51%H; 2.88%N; 14.91%Cl.

EXAMPLE 25

A mixture of 1.5 g of the free base 3-(3,4-dichlorophenyl)-1,3-dihydrospiro[benzo[c]thiophene-1,4'-piperidine] of Example 24, 1.3 g of γ-chlorobutyrophenone ethylene ketal, 0.9 g of potassium iodide, 0.9 g of sodium bicarbonate in 15 ml of anhydrous dimethylformamide is stirred at 80° C. for 16 hours. The mixture is diluted with ice-water and extracted three times with $CH_2Cl_2$. The $CH_2Cl_2$ solution is dried ($K_2CO_3$) and concentrated in vacuo to an oily residue. Purification is carried out by column chromatography (alumina-ether) and upon treatment with ethereal-HBr, a crystalline hydrobromide is obtained with simultaneous cleavage of the ketal ring. Recrystallization of the granular hydrobromide from methanol-ether gives colorless crystals of 3-(3,4-dichlorophenyl)-1'-[3-(4-fluorobenzoyl)-propyl]-1,3-dihydrospiro[benzo(c)thiophene-1,4'-piperidine]hydrobromide.

Analysis: Calculated for $C_{28}H_{26}Cl_2FNOS.HBr$: 56.47%C; 4.57%H; 2.23%N. Found: 56.43%C; 4.59%H; 2.31%N.

EXAMPLE 26

A mixture of the free base 3-(3,4-dichlorophenyl)-1,3-dihydrospiro[benzo[c]thiophene-1,4'-piperidine] of Example 24 (2.0 g), 1.8 g of γ-chloro-4-fluorobutyrophenone ethylene ketal, 0.9 g of sodium bicarbonate, 0.9 g of potassium iodide in 15 ml of anhydrous DMF is stirred at 80° C. for 16 hours. The cooled mixture is diluted with water and ether and the layers are separated. The organic solution is washed with water, dried ($MgSO_4$) and concentrated to an oily residue in vacuo. Purification of the crude product is accomplished by passing through a short alumina-ether column. Elution with ether gives a pale yellowish oil which is converted to a crystalline maleate in ether. Recrystallization from acetone-ether gives granulars, m.p. 116°–119° C. of 3-(3,4 dichlorophenyl)-1'-[3-(4-fluorobenzoyl)propyl]-1,3 dihydrospiro[benzo(c)thiophene-1,4'-piperidine]ethylene ketal maleate.

Analysis: Calculated for $C_{30}H_{30}Cl_2FNO_2S \cdot C_4H_4O_4$: 60.52%C; 5.08%H; 2.08%N. Found: 60.53%C; 5.05%H; 1.86%N.

EXAMPLE 27 a. A mixture of 4-(2-fluorophenyl)-4-hydroxy-1-methylpiperidine of Example 1a (10.5 g), 10 g of p-fluorobenzyl mercaptan, 18 ml of boron trifluoride etherate and 10 ml of glacial acetic acid is stirred at 60°–65° C. for 16 hours. The excess reagents are removed under reduced pressure at 100° and the oily residue is triturated with an excess of 0.5N hydrochloric acid and 200 ml of ether. A white precipitate is filtered after 2 hours at 5°–10° C. and is basified to give the desired product. The oily amine is converted to a crystalline maleate in ether, recrystallization from methanol-ether gives colorless prisms, m.p. 123°–125° C. of 4-(4-fluorobenzylthio)-4-(2-fluorophenyl)-1-methylpiperidine maleate.

Analysis: Calculated for $C_{19}H_{21}F_2NS \cdot C_4H_4O_4$: 61.45%C; 5.61%H; 3.12%N. Found: 61.71%C; 5.75%H; 3.15%N.

b. A solution of sodium methylsulfinyl methide is prepared by heating 0.87 g of sodium hydride in 80 ml of dimethylsulfoxide at 80° C. for 30 minutes. The solution is then treated with 8.9 g of the free base 4-(4-fluorobenzylthio)-4-(2-fluorophenyl)-1-methylpiperidine of Example 27a in 20 ml of DMSO over 2 minutes and stirring continued for 15 minutes at 80° C. before quenching with ice-water. The mixture is extracted 3 times with $CH_2Cl_2$, the combined $CH_2Cl_2$ solution washed with water and dried, and concentrated to an oily residue. Purification of the crude product is carried out by column chromatography (alumina-ether) and concentration of the combined effluent affords a heavy oil which crystallizes on cooling. Recrystallization from ether-pentane gives long needles, m.p. 109°–110° C., of 3-(4-fluorophenyl)-1,3-dihydro-1'-methylspiro[benzo(c)thiophene-1,4'-piperidine].

Analysis: Calculated for $C_{19}H_{20}FNS$: 72.81%C; 6.43%H; 4.47%N; 6.38%F. Found: 73.05%C; 6.31%H; 4.58%N; 6.23%F.

EXAMPLE 28

A mixture of 3-(4-fluorophenyl)-1,3-dihydro-1'-methylspiro[benzo(c)thiophene-1,4'-piperidine] of Example 27 (3.6 g), 2.1 g of phenyl chloroformate in 100 ml of $CH_2Cl_2$ is stirred at room temperature for 64 hours. The solution is washed with 10% aqueous NaOH, water, and dried over $MgSO_4$. Evaporation under reduced pressure affords a crystalline residue, m.p. 198°–200° C. Recrystallization of the crude product from acetone-pentane gives granular crystals, m.p. 200°–201° C. of 3-(4-fluorophenyl)-1,3-dihydro-1'-phenoxycarbonylspiro[benzo(c)thiophene-1,4'-piperidine].

Analysis: Calculated for $C_{25}H_{22}FNO_2S$: 71.57%C; 5.28%H; 3.34%N. Found: 71.73%C; 5.25%H; 3.20%N.

EXAMPLE 29

A mixture of 3-(4-fluorophenyl)-1,3-dihydro-1'-phenoxycarbonylspiro[benzo(c)thiophene-1,4'-piperidine] of Example 28 (4.3 g), 1.4 g of potassium hydroxide in 50 ml of ethylene glycol is stirred at 160° C. for 30 minutes. The cooled mixture is diluted with water and extracted three times with 150 ml portions of ether. The combined ether extract is washed with water (3–4 times), dried, and concentrated to an oily residue of secondary amine. The secondary amine is converted to its hydrochloride in a conventional manner by stirring without heating with hydrochloric acid for several hours. Recrystallization from methanol-acetone-ether gives crystals, m.p. 259°–260° C. of 3-(4-fluorophenyl)-1,3-dihydrospiro[benzo(c)thiophene-1,4'-piperidine]hydrochloride.

Analysis: Calculated for $C_{18}H_{18}FNS \cdot HCl$: 64.36%C; 5.70%H; 4.17%N; 5.65%F. Found: 64.09%C; 5.55%H; 4.28%N; 5.78%F.

EXAMPLE 30

A mixture of 3-(4-fluorophenyl)-1,3-dihydrospiro[benzo(c)thiophene-1,4'-piperidine] (2.2 g of the free base of Example 29) 2.2 g of γ-chloro-4-fluorobutyrophenone ethylene ketal, 1.5 g of sodium bicarbonate, 1.5 g of potassium iodide in 25 ml of DMF is stirred at 80° C. for 16 hours. The cooled mixture is quenched with water, extracted 3 times with ether and dried. Removal of the solvent in vacuo at 80° C. leaves a reddish oil which is purified by passing through a short column of alumina packed in ether. Elution with ether gives a pure tertiary amine which is converted into a crystalline maleate. Recrystallization from acetone-ether affords colorless prisms, m.p. 175°–177° C. of 1'-[3-(4-fluorobenzoyl)propyl]-3-(4-fluorophenyl)-1,3-dihydrospiro[benzo(c)thiophene-1,4'-piperidine]ethylene ketal maleate.

Analysis: Calculated for $C_{30}H_{31}F_2NO_2S \cdot C_4H_4O_4$: 65.46%C; 5.64%H; 2.24%N. Found: 65.28%C; 5.71%H; 2.21%N.

EXAMPLE 31

A solution of 1'-[3-(p-fluorobenzoyl)propyl]-3-(4-fluorophenyl)-1,3-dihydro-spiro[benzo(c)thiophene-1,4'-piperidine]ethylene ketal of Example 30 (2.3 g of the free base) in 200 ml of ether and 10 ml of methanol is saturated with anhydrous hydrogen bromide. After standing at room temperature for 2 hours, the mixture is carefully neutralized with 1N ammonia and the ether solution is washed 3 times with water, dried and concentrated to an oily residue. The free base is converted to a crystalline maleate in ether and recrystallization from acetone-ether gives off-white prisms, m.p. 149°–150° C., of 1'-[3-(4-fluorobenzoyl)propyl]-3-(4-fluorophenyl)-1,3-dihydrospiro[benzo(c)thiophene-1,4'-piperidine]maleate.

Analysis: Calculated for $C_{28}H_{27}F_2NOS \cdot C_4H_4O_4$: 66.31%C; 5.40%H; 2.42%N; 6.55%F. Found: 66.41%C; 5.22%H; 2.36%N; 6.64%F.

EXAMPLE 32 a. 59.7 g of 2-chlorobenzylmercaptan, followed by 55 ml of boron trifluoride etherate are added to 25 g of 4-(2-fluorophenyl)-4-hydroxy-1-methylpiperidine of Example 1a in 55 ml of acetic acid. The reaction is stirred at 55°–65° C. for 20 hours. The excess acid is removed under reduced pressure at 80°–100° C. The oily residue is then equilibrated with 200 ml of 2N hydrochloric acid and 200 ml of ether. The ether, and two more 125 ml portions of ether, is decanted off. The oil and water mixture is diluted to 650 ml volume with water and is stored at 0° C. for about three days to produce crystals. The mixture is diluted and filtered. The precipitate is washed with water and ether, and dried. The solid is recrystallized (acetone:ether) to a broad melting (122°–129° C.) solid. A portion of the solid is placed in water, basified with 10% aqueous NaOH, extracted into ether, washed, dried and treated with ethereal hydrogen chloride to give a white powder. The powder is recrystallized from acetone-ether to give a white crystalline solid, m.p. 173°–175° C. of 4-(2-chlorobenzylthio)-4-(2-fluorophenyl)-1-methylpiperidine hydrochloride.

Analysis: Calculated for $C_{19}H_{21}ClFNS$: 59.08%C; 5.74%H; 3.63%N; 4.92%F. Found: 58.81%C; 5.63%H; 3.37%N; 5.03%F.

b. A 0.2 g portion of sodium hydride (prepared by washing a 50% oil dispersion) is heated at 80° C. with stirring in 15 ml of dry dimethylsulfoxide for 30 minutes. Then 2.1 g of the free base 4-(2-chlorobenzylthio)-4-(2-fluorophenyl)-1-methylpiperidine of Example 32a in 10 ml of dry DMSO is added in one portion and the oil bath is removed. The reaction is allowed to stir without heating for 40 minutes, then is poured onto 250 cc of ice with 250 ml of ether. The layers are shaken and separated and the aqueous portion extracted again with 150 ml of ether. The combined ether is washed with two 100 ml portions of water and one 10 ml portion of saturated sodium chloride solution, and is dried over magnesium sulfate to give an oil. The oil is chromatographed on a column of alumina with ether to a material (free base) showing one spot (Rf 0.54; 25% MeOH:$CH_2Cl_2$, silica) by tlc. The product in ether is treated with excess ethereal maleic acid, washed with ether, and dried to give a white powder, m.p. 173°–176° C., of 3-(2-chlorophenyl)-1,3-dihydro-1'-methylspiro[benzo(c)thiophene-1,4'-piperidine]maleate.

A small portion of the salt is recrystallized twice from acetone to give crystals melting at 178°–178.5° C.

Analysis: Calculated for $C_{19}H_{20}ClNS.C_4H_4O_4$: 61.95%C; 5.43%H; 3.14%N; 7.95%Cl. Found: 62.03%C; 5.46%H; 3.10%N; 7.94%Cl.

EXAMPLE 33 a. A mixture of 4-(2-fluorophenyl)-4-hydroxy-1-methylpiperidine of Example 1a (15.8 g), 12 ml of 2-fluorobenzyl mercaptan and 20 ml of boron trifluoride etherate in 15 ml of glacial acetic acid is stirred at 65°–70° C. for 16 hours. The excess reagents are removed under reduced pressure, the residue is triturated with 300 ml of 0.5N HCl and 100 ml of ether. After standing at 5°–10° C. for 30 minutes, a crystalline precipitate is filtered, air dried and made basic with 10% aqueous $NH_4OH$. The liberated amine is taken up in ether, dried and concentrated to a yellowish oil which is then converted to its maleate in ether, recrystallization of the crude salt from methanol-ether gives colorless prisms, m.p. 153°–154° C. of 4-(2-fluorobenzylthio)-4-(2-fluorophenyl)-1-methylpiperidine maleate.

Analysis: Calculated for $C_{19}H_{21}F_2NS.C_4H_4O_4$: 61.45%C; 5.61%H; 3.12%N. Found: 61.28%C; 5.57%H; 2.98%N.

b. A solution of sodium methylsulfinyl methide is prepared by heating 1.2 g of sodium hydride in 100 ml of DMSO at 80° C. for 30 minutes. The mixture is cooled to room temperature and to it is added 12 g of the free base 4-(2-fluorobenzylthio)-4-(2-fluorophenyl)-1-methylpiperidine in 40 ml of DMSO over a period of 5 minutes. Following the addition, the mixture is stirred at 70°–80° C. for an additional 30 minutes. The mixture is diluted with ice-water, extracted 3 times with ether. The combined ether solution is washed 4 times with water, dried and concentrated to a thick oil. Chromatography over $Al_2O_3$-ether removes a small amount of impurities and the purified amine is converted to a crystalline hydrobromide in ether. Recrystallization from methanol-ether gives colorless crystals, m.p. 263°–265° (dec.) of 3-(2-fluorophenyl)-1,3-dihydro-1'-methylspiro[benzo(c)thiophene-1,4'-piperidine]hydrobromide.

Analysis: Calculated for $C_{19}H_{20}FNS.HBr$: 57.86%C; 5.37%H; 3.55%N; 4.82%F. Found: 57.67%C; 5.47%H; 3.58%N; 4.80%F.

EXAMPLE 34

A mixture of the free amine 3-(2-fluorophenyl)-1,3-dihydro-1'-methylspiro[benzo(c)thiophene-1,4'-piperidine] of Example 33 (6.3 g), 3.9 g of phenyl chloroformate in 100 ml of anhydrous $CH_2Cl_2$ is stirred at room temperature for 4 hours. The reaction mixture is washed with 10% aqueous sodium hydroxide and dried over $MgSO_4$ for 2 hours.

Removal of solvent under reduced pressure leads to a thick oil which is purified through a short silica gel column packed in $CH_2Cl_2$. Elution with a large excess of $CH_2Cl_2$ gave, after concentration, a colorless oil which solidified on standing, to yield 3-(2-fluorophenyl)-1,3-dihydro-1'-phenoxycarbonylspiro[benzo(c)thiophene-1,4'-piperidine] m.p. 122°–123° C.

Analysis: Calculated for $C_{25}H_{22}FNO_2S$: 71.57%C; 5.28%H; 3.34%N. Found: 71.49%C; 5.23%H; 3.27%N.

EXAMPLE 35

A mixture of 3-(2-fluorophenyl)-1,3-dihydro-1'-phenoxycarbonylspiro[benzo(c)thiophene-1,4'-piperidine] of Example 34 (5.6 g), 18 g of potassium hydroxide in 100 ml of ethylene glycol is stirred at 170° C. for 30 minutes. The mixture is poured into water and extracted 3 times with ether. The ether solution is washed with water, dried and concentrated in vacuo to give a viscous oil of free amine. A crystalline maleate is prepared and recrystallized from methanol-acetone-ether to give a white powder of 3-(2-fluorophenyl)-1,3-dihydrospiro[benzo(c)thiophene-1,4'-piperidine]maleate.

Analysis: Calculated for $C_{18}H_{18}FNS.C_4H_4O_4$: 63.59% C; 5.34%H; 3.37%N; 4.57%F. Found: 63.55%C; 5.33%H; 3.10%N; 4.52%F.

EXAMPLE 36

A mixture of 3-(2-fluorophenyl)-1,3-dihydrospiro[benzo(c)thiophene-1,4'-piperidine] of Example 35 (2.2 g), 2.2 g of γ-chloro-4-fluorobutyrophenone ethylene ketal compound, 1.5 g of potassium iodide, 1.5 g of sodium bicarbonate in 25 ml of DMF is stirred at 70°–75° C. for 16 hours. The cooled mixture is diluted with water and the mixture extracted 3 times with ether. The ether solution, after washing with water and drying, is concentrated in vacuo to an oily residue which is purified through a short column of alumina, elution with ether gives a colorless oil which is converted to a crystalline maleate, m.p. 105°–151° C. of 1'-[3-(4-fluorobenzoyl)propyl]-3-(2-fluorophenyl)-1,3-dihydrospiro[benzo(c)thiophene-1,4'-piperidine]ethylene ketal maleate.

Analysis: Calculated for $C_{30}H_{31}F_2NO_2S.C_4H_4O_4$: 65.46%C; 5.64%H; 2.24%N. Found: 65.46%C; 5.37%H; 2.12%N.

EXAMPLE 37

A solution of 1'-[3-(4-fluorobenzoyl)propyl]-3-(2-fluorophenyl)-1,3-dihydrospiro[benzo(c)thiophene-1,4'-piperidine]ethylene ketal of Example 36 (2.0 g) in 20 ml of ethanol and 20 ml of 3N hydrochloric acid is heated on a steam bath for 30 minutes. The cooled solution is basified with 40% aqueous sodium hydroxide and extracted 3 times with ether. The combined ether solution is washed thoroughly with water, dried and treated with an excess of ethereal maleic acid. A crystalline maleate is recrystallized from acetone-ether to give all-white prisms, m.p. 137°–138.5° C., of 1'-[3-(4-fluorobenzoyl)propyl]-3-(2-fluorophenyl)-1,3-dihydrospiro[benzo(c)thiophene-1,4'-piperidine]maleate.

Analysis: Calculated for $C_{28}H_{27}F_2NO \cdot C_4H_4O_4$: 66.31%C; 5.40%H; 2.42%N; 6.55%F. Found: 66.18%C; 5.34%N; 2.42%N; 6.49%F.

EXAMPLE 38

A 4.5 g sample of phenyl chloroformate in 150 ml of dichloromethane is stirred at 25° C. while 7.5 g of 1,3-dihydro-1'-methyl-3-(2-methylphenyl)spiro[benzo(c)-thiophene-1,4'-piperidine] of Example 23 in 75 ml of dichloromethane is rapidly added. The reaction is stirred a total of 24 hours at 25° C. and quenched with 225 ml of 10% aqueous NaOH solution. The organic layer is separated, washed with water, dried over MgSO$_4$, filtered and evaporated to an oil. The oil is column chromatographed on a silica gel/CH$_2$Cl$_2$ column with CH$_2$Cl$_2$ being used for elution. The isolated product is a pale yellow oil of 1,3-dihydro-3-(2-methylphenyl)-1'-phenoxycarbonylspiro[benzo(c)thiophene-1,4'-piperidine].

Analysis: Calculated for $C_{26}H_{25}NO_2S$: 75.15%C; 6.06%H. Found: 74.90%C; 6.05%H.

EXAMPLE 39

A solution of 16 g of potassium hydroxide dissolved in 100 ml of ethylene glycol is added to 6.0 g of 1,3-dihydro-3-(2-methylphenyl)-1'-phenoxycarbonylspiro[-benzo(c)thiophene-1,4'-piperidine] of Example 38. The resulting solution is stirred and heated at 160° C. for one hour. The solution is poured into 300 ml of ice water and extracted with ether. The ether fractions are combined, washed with water, dried over MgSO$_4$, filtered, and evaporated to a residue which is converted to a white, granular, maleate salt, 1,3-dihydro-3-(2-methylphenyl)spiro[benzo(c)thiophene-1,4'-piperidine]maleate, which is recrystallized from methanol-ether and has a m.p. 178°–179° C.

Analysis: Calculated for $C_{19}H_{21}NS \cdot C_4H_4O_4$: 67.13%C; 6.12%H; 3.40%N. Found: 67.10%C; 5.96%H; 3.14%N.

EXAMPLE 40

A mixture of 6.0 g of 1,3-dihydro-3-(4-methylphenyl)-1'-phenoxycarbonylspiro[benzo(c)thiophene-1,4'-piperidine] of Example 13, 16.0 g of potassium hydroxide and 100 ml of ethylene glycol is stirred and heated at 160° C. for one hour. The reaction mixture is quenched with ice water and extracted with ether. The ether extracts are combined, washed with water, dried over MgSO$_4$, and evaporated to an oil. The oil is converted to 1,3-dihydro-3-(4-methylphenyl)spiro[benzo(c)thiophene-1,4'-piperidine]maleate. m.p. 214°–215° C.

Analysis: Calculated for $C_{19}H_{21}NS \cdot C_4H_4O_4$: 67.13%C; 6.12%H; 3.40%N. Found: 67.05%C; 6.20%H; 3.21%N.

EXAMPLE 41 a. To 25 g of 4-(2-fluorophenyl)-4-hydroxyl-1-methylpiperidine of Example 1a is added 50 g of m-methylbenzyl mercaptan. To this mixture is added 68 ml of boron trifluoride etherate. The reaction is stirred at 65°–70° C. for about three days. Excess reagent is then removed under aspirator pressure at 60°–100° C. The mixture is poured into 360 ml of 0.5N hydrochloric acid with 300 ml of ether. An oil falls out, from which the water and ether are decanted. The oil is placed under 250 ml of 0.5N hydrochloric acid and 200 ml of ether. The oil is again separated from the solutions and is placed under 150 ml of water with 20 ml of 10% aqueous sodium hydroxide solution. The suspension is diluted further with 200 ml of water and is extracted with two 200 ml portions and one 100 ml portion of ether. The combined amine ether extracts are added to a solution of 12.5 ml of 48% aqueous hydrogen bromide in 300 ml of water to give a white salt. The mixture is allowed to stand 16 hours, then the ether is decanted off. The aqueous mixture is washed again by adding and decanting 200 ml of ether. The salt is then filtered off, washed with water and ether, and dried to a white powder, m.p. 143°–145° C., of 4-(2-fluorophenyl)-4-(3-methylbenzylthio)-1-methylpiperidine hydrobromide. A thrice recrystallized (acetone-ether) sample melts at 145°–146° C.

Analysis: Calculated for $C_{20}H_{24}FNS \cdot HBr$: 58.54%C; 6.14%H; 3.41%N. Found: 58.45%C; 6.16%H; 3.16%N.

b. A 3.43 g portion of 50% sodium hydride dispersion is washed with hexane under dry nitrogen and then heated with 100 ml of sieve dried dimethylsulfoxide at 80°–85° C. for 40 minutes. Then 18.48 g of the free base of 4-(2-fluorophenyl)-4-(3-methylbenzylthio)-1-methylpiperidine of Example 41a in 70 ml of dry DMSO is added over 60 seconds. The red mixture is stirred, cooled to room temperature over one hour, and poured into 500 cc of ice water. The aqueous mixture is extracted with three 200 ml portions of dichloromethane. Combined dichloromethane extracts are washed with four 200 ml portions of water and one 100 ml portion of saturated aqueous sodium chloride solution; and dried over magnesium sulfate to yield an oil. The oil is dissolved in ether, filtered, evaporated, and chromatographed on 400 ml of alumina with ether to give an oil which is dissolved in ether and treated with ethereal hydrogen bromide to give a salt. The salt is washed with ether and recrystallized from methanol-acetone-ether to give a white, crystalline powder, m.p. 258°–260° C. of 1,3-dihydro-1'-methyl-3-(3-methylphenyl)spiro[benzo(c)thiophene-1,4'-piperidine]hydrobromide.

Analysis: Calculated for $C_{20}H_{23}NS \cdot HBr$: 61.54%C; 6.20%H; 3.59%N. Found: 61.27%C; 6.24%H; 3.45%N.

EXAMPLE 42

A solution of 0.70 g of the amine 1,3-dihydro-3-(2-methylphenyl)spiro[benzo(c)thiophene-1,4'-piperidine] of Example 39, 0.76 g of γ-chloro-p-fluorobutyrophenone ethylene ketal, 0.38 g of sodium bicarbonate, 0.38 g of KI, and 10 ml of anhydrous DMF is stirred and heated at 70°–80° C. for 24 hours. The reaction is worked up by pouring it into water and extracting with ether. The ether fractions are combined, washed with water, and dried over MgSO$_4$. The solution is filtered, evaporated and the resulting oil column chromatographed on a Al$_2$O$_3$/ether column (eluted with ether). The isolated product is converted to a maleate salt of 1'-[3-(4-fluorobenzoyl)propyl]-1,3-dihydro-3-(2-methylphenylspiro[benzo(c)thiophene-1,4'-piperidine]ethylene ketal maleate, m.p. 157°–159° C.

Analysis: Calculated for $C_{31}H_{34}FNO_2S \cdot C_4H_4O_4$: 67.83%C; 6.18%H; 2.26%N. Found: 67.78%C; 6.02%H. 2.24%N.

EXAMPLE 43

To 3.83 g of phenyl chloroformate in 850 ml of dichloromethane is added a solution of 6.73 g of the free base 3-(2-chlorophenyl)-1,3-dihydro-1'-methylspiro[benzo(c)thiophene-1,4'-piperidine] of Example 32 in 75 ml of dichloromethane over two minutes. The reaction is stirred at ambient temperature for 64 hours, then diluted with 200 ml of dichloromethane and washed with two 300 ml portions of 5% aqueous sodium hydroxide solution, two 200 ml portions of water and one 75 ml portion of brine. The solution is dried over magnesium sulfate and evaporated in an oil. The oil is chromatographed on a silica gel with dichloromethane to given an oil of 3-(-2-chlorophenyl)-1,3-dihydro-1'-phenoxycarbonylspiro[benzo(c)thiophene-1,4'-piperidine].

Analysis: Calculated for $C_{25}H_{22}ClNO_2S$: 68.88%C; 5.09%H; 3.21%N. Found: 69.36%C; 4.94%H; 3.33%N.

EXAMPLE 44

To 1.81 g of phenyl chloroformate in 40 ml of dichloromethane is added a solution of 2.98 g of the free base 1,3-dihydro-1'-methyl-3-(3-methylphenyl)spiro[benzo(c)thiophene-1,4'-piperidine] of Example 41 in 35 ml of dichloromethane over 5 minutes. The reaction is stirred at ambient temperature for 21 hours The reaction is then diluted with 100 ml of dichloromethane; washed with two 150 ml portions of 5% aqueous sodium hydroxide solution, two 100 ml portions of water and one 50 ml portion of brine; and dried over magnesium sulfate to an oil. The oil is chromatographed on silica gel with dichloromethane to yield 1,3-dihydro-3-(3-methylphenyl)-1'-phenoxycarbonylspiro[benzo(c)-thiophene-1,4'-piperidine], m.p. 154°–157° C. A portion is recrystallized from toluene-hexane, m.p. 157°–160° C.

Analysis: Calculated for $C_{26}H_{25}NO_2S$: 75.16%C; 6.07%H; 3.37%N. Found: 75.28%C; 6.12%H; 3.17%N.

EXAMPLE 45

To 6.19 g of 3-(-2-chlorophenyl)-1,3-dihydro-1'-phenoxycarbonylspiro[benzo(c)thiophene-1,4'-piperidine] of Example 43 in 95 ml of ethylene glycol at 150° C. is added 15.1 g of 85% potassium hydroxide pellets. The reaction is stirred in a 160°–165° C. bath for 40 minutes, then cooled to room temperature and poured into 250 ml of water. The mixture is diluted to 500 ml with water and extracted with three 150 ml portions of water and one 40 ml portion of saturated sodium chloride solution and dried over magnesium sulfate to an oil. The oil is dissolved in ether, filtered, and treated with ethereal maleic acid. The crude salt is washed with ether and recrystallized from methanol-acetone-ether to give a white salt of 3-(2-chloroethyl)-1,3-dihydrospiro[benzo(c)thiophene-1,4'-piperidine]maleate, m.p. 172°–173° C.

Analysis: Calculated for $C_{18}H_{18}ClNS$: 61.18%C; 5.14%H; 3.24%N; 8.21%Cl. Found: 61.47%C; 5.22%H; 3.18%N; 7.85%Cl.

EXAMPLE 46

To 2.48 g of the free base, 3-(2-chlorophenyl)-1,3-dihydro-spiro[benzo[c]thiophene-1,4'-piperidine] of Example 45, in 28 ml of sieve-dried dimethylformamide with 2.78 g of γ-chloro-p-fluorophenylbutyrophenone ethylene ketal is added 2.02 g of sodium bicarbonate and 2.02 g of potassium iodide. The reaction is then heated in an 85°–50° C. bath for 17 hours. The mixture is diluted with 90 ml of chloroform and filtered through paper. The solution is evaporated and the oil partitioned between 140 ml of dichloromethane and 75 ml of water. The dichloromethane is washed with 75 ml of water and one 25 ml portion of saturated sodium chloride solution and dried over magnesium sulfate. The oil is chromatographed on alumina with ether and treated with ethereal oxalic acid to give a salt. The salt is washed with ether and recrystallized from methanol-acetone-ether (m.p. 200°–201° C.) to give a white solid of 3-(2-chlorophenyl)-1'-[3-(4-fluorobenzoyl)propyl]-1,3-dihydrospiro[benzo(c)thiophene-1,4'-piperidine]ethylene ketal oxalate, m.p. 200°–201° C.

Analysis: Calculated for $C_{30}H_{31}ClFNO_2S \cdot C_2H_2O_4$: 62.59%C; 5.42%H; 2.28%N. Found: 62.53%C; 5.44%H; 2.26%N.

EXAMPLE 47 a. To 14.45 g of 4-(2-fluorophenyl)-4-hydroxy-1-methylpiperidine of Example 1a is added 39.45 g of 2,4-dichlorobenzyl mercaptan followed by 40 ml of boron trifluoride etherate. The reaction is stirred at 80°–85° C. for about 4 days. The excess reagent is removed under aspirator pressure to 110° C. and the residual oil poured into 200 ml of 0.5N hydrochloric acid and 200 ml of ether. The mixture is allowed to stand 18 hours, the ether decanted off and two more 200 ml portions of ether are added and decanted. The crude precipitate is filtered, washed with 75 ml of water and three 125 ml portions of ether, and dried to an apparently mixed salt. A portion of the salt is basified in aqueous ammonium hydroxide, extracted with ether, washed with water and brine, and dried over magnesium sulfate. The ethereal solution is treated with ethereal hydrogen bromide to give a salt. The salt is washed with ether and dried to give a white powder of 4-(2,4-dichlorobenzylthio)-4-(2-fluorophenyl)-1-methylpiperidine hydrobromide, m.p. 208.5°–210° C.

Analysis: Calculated for $C_{19}H_{20}Cl_2FNS \cdot HBr$: 49.05%C; 4.55%H; 3.01%N. Found: 48.87%C; 4.52%H; 2.96%N.

b. A 0.3 g of sodium hydride (50%) is washed with hexane nitrogen and heated at 80° C. with 11 ml of dry dimethylsulfoxide for 30 minutes. Then 1.68 g of the free base, 4-(2,4-dichlorobenzylthio)-4-(2-fluorophenyl)-1-methylpiperidine of Example 47a in 7.3 ml of dry DMSO is added at once and the heating removed. The reaction is stirred under nitrogen, while cooling to room temperature over 45 minutes, then poured onto ice and extracted with 50 ml of ether and 1 50 ml of dichloromethane. Combined organic phases are washed with two 100 ml portions of water and one 25 ml portion of brine, and dried over magnesium sulfate to an oil. The oil is chromatographed on alumina with ether to give an oil. The oil, in ether, is treated with ethereal hydrogen bromide to form a salt. The salt is washed with ether and recrystallized from acetone-ether to give a yellowish-white salt of 3-(2,4-dichlorophenyl)-1,3-dihydro-1'-methyl-spiro(benzo(c)thiophene-1,4'-piperidine)hydrobromide, m.p. 259.5°–261° C. A portion of the crude salt is recrystallized thrice from methanol-acetone ether to give a m.p. 260°–261° C.

Analysis: Calculated for $C_{19}H_{19}Cl_2NS \cdot HBr$: 51.26%C; 4.53%H; 3.15%N; 15.93%Cl. Found: 51.43%C; 4.56%H; 3.15%N; 15.65%Cl.

EXAMPLE 48

To 1.34 g of 1,3-dihydro-3-(3-methylphenyl)-1'-phenoxycarbonylspiro[benzo(c)thiophene-1,4'-piperidine] of Example 44 in 22 ml of ethylene glycol, under nitrogen, at 150° C. is added 3.44 g of 85% aqueous potassium hydroxide. The reaction is stirred at 160° C. for 40 minutes, then is poured into 50 ml of ice water, diluted to 120 ml and extracted with two 50 ml portions of dichloromethane. The combined dichloromethane extract is washed with two 50 ml portions of water and one 20 ml portion of saturated sodium chloride solution, and dried over magnesium sulfate to an oil. The oil is purified by swirling and decanting one 50 ml portion and two 25 ml portions of boiling hexane. The evaporated hexane gives an oil (free base) which is dissolved in ether, treated with ethereal maleic acid, and recrystallized from acetone to a white powder of 1,3-dihydro-3-(3-methylphenyl)spiro[benzo(c)thiophene-1,4'-piperidine]maleate, m.p. 175°–176° C.

Analysis: Calculated for $C_{19}H_{21}SN.C_4H_4O_4$: 67.14%C; 6.12%H; 3.41%N. Found: 67.29%C; 6.13%H; 3.30%N.

EXAMPLE 49

To 4.02 g of the free base 3-(2-chlorophenyl)-1'-[3-(4-fluorobenzoyl)propyl]-1,3-dihydrospiro[benzo(c)thiophene-1,4'-piperidine]ethylene ketal of Example 46 in 250 ml of ether with 15 ml of methanol is added 120 ml of an ethereal hydrogen bromide solution. The reaction is allowed to stir for two hours, then 120 ml of 1:4, 58% ammonium hydroxide:water is added with stirring to dissolve all material. The layers are separated and the ether washed with three 100 ml portions of water and one 25 ml portion of saturated aqueous sodium chloride solution and dried over magnesium sulfate to yield a solid. The solid is stirred in a mixture of 125 ml of ether and 64 ml of 15:1, water:58% ammonium hydroxide for one hour. The layers are separated and the aqueous layer washed with two 50 ml portions of ether, and then filtered and dried to a solid. The combined ether solutions are washed with water and brine, dried, evaporated, and the solids recrystallized from ethyl acetate and combined to give a solid of 3-(2-chlorophenyl)-1'-[3-(4-fluorobenzoylpropyl]dihydrospiro[benzo(c)thiophene-1,4'-piperidine], melting at 144°–148° C.

Analysis: Calculated for $C_{28}H_{27}ClFNOS$: 70.07%C; 5.67%H; 2.92%N; 7.39%Cl. Found: 69.81%C; 5.54%H; 2.79%N; 7.29%Cl.

EXAMPLE 50

To 5.25 g of the free base, 1,3-dihydro-3-(3-methylphenyl)spiro[benzo(c)thiophene-1,4'-piperidine] of Example 48, in 65 ml of sieve-dried dimethylformamide is added 5.43 g of γ-chloro-p-fluorobutyrophenone ethylene ketal, followed by 3.6 g of sodium bicarbonate and 3.6 g of potassium iodide. The reaction is stirred in an 85° C. bath for 24 hours, then diluted with 130 ml of chloroform and filtered. The solvent is removed and the residual oil is partitioned between 250 ml of dichloromethane and 150 ml portion of water and one 35 ml portion of saturated sodium chloride solution and dried over magnesium sulfate to an oil. The oil is chromatographed on alumina with ether and is converted to the maleate salt by treatment with ethereal maleic acid. Recrystallization from acetone-ether yields 1'-[3-(4-fluorobenzoyl)propyl]-1,3-dihydro-3-(3-methylphenyl)spiro[benzo(c)thiophene-1,4'-piperidine]ethylene ketal maleate, m.p. 155°–157° C.

Analysis: Calculated for $C_{31}H_{34}FNO_2S.C_4H_4O_4$: 67.84%C; 6.18%H; 2.26%N. Found: 67.76%C; 6.19%H; 2.15%N.

EXAMPLE 51

To 8.5 g of phenyl chloroformate in 130 ml of dry dichloromethane under nitrogen is added a solution of 15.56 g of the free base of 3-(2,4-dichlorobenzylthio)-1,3-dihydro-1'-methylspiro[benzo(c)thiophene-1,4'-piperidine] of Example 47 in 100 ml of dry dichloromethane over 15 minutes. The reaction is stirred at ambient temperature for 21 hours, then diluted with 450 ml of dichloromethane, washed with two 300 ml portions of 10% aqueous sodium hydroxide solution, two 300 ml portions of water and one 100 ml portion of brine and dried over magnesium sulfate to an oil. The oil is chromatographed on silica gel with dichloromethane to give a clear oil of 3-(2,4-dichlorophenyl)-1,3-dihydro-1'-phenoxycarbonylspiro[benzo(c)thiophene-1,4'-piperidine].

Elemental Analysis: Calculated for $C_{25}H_{21}Cl_2NO_2S$: 63.84%C; 4.50%H; 2.98%N. Found: 63.71%C; 4.52%H; 2.79%N.

EXAMPLE 52

A solution of 2.85 g of the free base 1'-[3-(4-fluorobenzoyl)propyl]-1,3-dihydro-3-(2-methylphenyl)-spiro[benzo(c)thiophene-1,4'-piperidine]ethylene ketal of Example 42, 30 ml of absolute ethanol, and 30 ml of 3N HCl solution is refluxed for 45 minutes. The reaction is cooled, made basic with 40% aqueous NaOH solution, and extracted with $CH_2Cl_2$. The $CH_2Cl_2$ fractions are combined, washed with water, and dried over $MgSO_4$. The solution is filtered and evaporated to a solid which is recrystallized from ethyl acetate to give a pure product of 1'-[3-(4-fluorobenzoyl)propyl]-1,3-dihydro-3-(2-methylphenyl)spiro[benzo(c)thiophene-1,4'-piperidine], m.p. 143°–145° C.

Analysis: Calculated for $C_{29}H_{30}FNOS$: 75.78%C; 6.58%H; 3.05%N. Found: 75.51%C; 6.70%N; 2.85%N.

EXAMPLE 53

To 15.12 g of 3-(2,4-dichlorophenyl)-1,3-dihydro-1'-phenoxycarbonylspiro[benzo(c)thiophene-1,4'-piperidine] of Example 51 in 216 ml of ethylene glycol at 150° C., under nitrogen, is added 34.2 g of 85% potassium hydroxide pellets. The reaction is stirred at 160° C. for 45 minutes, then poured into 1.4 l of water and extracted with three 350 ml portions of dichloromethane. The combined dichloromethane extract is washed with two 400 ml portions of water and one 100 ml portion of saturated aqueous sodium chloride solution and dried over magnesium sulfate to an oil. The oil is purified by decanting with three 225 ml portions of boiling hexane to yield a solid. A portion of the solid is dissolved in ether and treated with ethereal maleic acid to give a salt. The salt is washed with ether and recrystallized from methanol-acetone-ether to a white powder of 3-(2,4-dichlorophenyl)-1,3-dihydrospiro[benzo(c)thiophene-1,4'-piperidine]maleate, m.p. 171°–172.5° C.

Analysis: Calculated for $C_{18}H_{17}Cl_2NS.C_4H_4O_4$: 56.66%C; 4.54%H; 3.00%N; 15.20%Cl. Found: 56.49%C; 4.54%H; 2.81%N; 14.99%Cl.

EXAMPLE 54

To 3.0 g of the free base 3-(2,4-dichlorophenyl)-1,3-dihydrospiro[benzo(c)thiophene-1,4'-piperidine] of Example 53 in 35 ml of sieve-dried dimethylformamide is added 2.62 g of γ-chloro-p-fluorobutyrophenone ethylene ketal, followed by 1.7 g of sodium bicarbonate and 1.7 g of potassium iodide. The reaction is stirred at 80°–90° C. for 20 hours. The mixture is diluted with 75 ml of chloroform, filtered, and rotary evaporated at 75° C. to an oil. The oil is partitioned between 125 ml of dichloromethane and 85 ml of water. The mixture is diluted with 10 ml of saturated aqueous sodium bicarbonate solution, and the organic layer separated and washed with one 80 ml portion of water and one 30 ml portion of saturated sodium chloride solution. The dichloromethane solution is dried and evaporated to an oil. The oil is chromatographed on alumina with ether and a portion of the resultant oil is placed in ether and treated with ethereal oxalic acid to give a salt. The salt is washed with ether and recrystallized from methanol-acetone-ether to yield a white powder of 3-(2,4-dichlorophenyl)-1'-[3-(4-fluorobenzoyl)propyl]-1,3-dihydrospiro[benzo(c)thiophene-1,4'-piperidine]ethylene ketal oxalate, m.p. 164°–165° C.

Analysis: Calculated for $C_{30}H_{30}Cl_2FNO_2S.C_2H_2O_4$: 59.26%C; 4.97%H; 2.16%N. Found: 59.15%C; 4.81%H; 2.11%N.

EXAMPLE 55 a. To 26.33 g of 4-(2-fluorophenyl)-4-hydroxy-1-methylpiperidine of Example 1a with 20 ml (approximately 23.3 g) of m-fluorobenzylmercaptan in 25 ml of glacial acetic acid is added 33 ml of boron trifluoride etherate. The reaction is stirred at 65°–68° C. for 44 hours, then an additional 17 ml of boron trifluoride etherate is added and stirring at 65°–68° C. is resumed for about three more days. Excess solvent is removed under reduced pressure to 110° C. The residue is mixed with 450 ml of 0.5N HCl and 175 ml of ether to form an oil. The oil and water layer is washed by decanting with ether, then the aqueous acid is carefully decanted from the oil. The oil is placed under water, treated to pH=9–10 with ammonium hydroxide and extracted with ether. The ethereal solution is washed with water until neutral, then is poured into a solution of 30 ml of 48% hydrogen bromide diluted to 350 ml to form a salt. The salt is filtered off, washed with a small amount of water and a generous amount of ether to give a white salt of 4-(3-fluorobenzylthio)-4-(2-fluorophenyl)-1-methylpiperidine hydrobromide, m.p. 176°–178.5° C. A thrice recrystallized (methanol-acetone-ether) sample melts at 178°–179.5° C.

Analysis: Calculated for $C_{19}H_{21}F_2NS.HBr$: 55.08%C; 5.35%H; 3.38%N. Found: 55.05%C; 5.38%H; 3.38%N.

b. To 1.404 g of sodium hydride (from 2.37 g of a 50% dispersion), under nitrogen, is added 120 ml of sieve-dried dimethylsulfoxide. The mixture is stirred in an 80°–85° C. bath for 35 minutes, then cooled to room temperature. A solution of 14.0 g of the free base 4-(3-fluorobenzylthio)-4-(2-fluorophenyl)-1-methylpiperidine of Example 55a in 47 ml of DMSO is added over 60 seconds and the solution stirred for one hour. The reaction is then poured into 700 ml of ice water and extracted with three 200 ml portions of dichloromethane. The combined dichloromethane extracts are washed with three 300 ml portions of water and one 75 ml portion of saturated sodium chloride solution, and dried over magnesium sulfate to an oil. The oil is chromatographed on alumina with ether to give crystals. A portion of this, in ether is treated with ethereal maleic acid. The resulting salt is washed with ether and dried to give a powder of 3-(3-fluorophenyl)-1,3-dihydro-1'-methylspiro[benzo(c)thiophene-1,4'-piperidine]maleate, m.p. 137°–140° C. A twice recrystallized portion melts at 138.5°–140.5° C. Upon continued heating, a new crystalline form develops which collapses in the 175°–180° C. range.

Analysis: Calculated for $C_{19}H_{20}FNS.C_4H_4O_4$: 64.32%C; 5.63%H; 3.26%N; 4.42%F. Found: 64.26%C; 5.58%H; 2.95%N; 4.58%F.

EXAMPLE 56

To 3.26 g of the free base 3-(2,4-dichlorophenyl)-1'-[3-(4-fluorobenzoyl)propyl]-1,3-dihydrospiro[benzo(c)thiophene-1,4'-piperidine]ethylene ketal of Example 54 in 30 ml of warm ethanol is slowly added 30 ml of 3N hydrochloric acid. The mixture is heated over a steam bath for 45 minutes. 10 ml of additional ethanol is added and heating is resumed for 45 minutes. The reaction is then cooled to room temperature and basified with 40% aqueous sodium hydroxide solution. The mixture is diluted with 200 ml of water and extracted with three 80 ml portions of dichlorothane. The combined dichloromethane extracts are washed with two 100 ml portions of water, one 50 ml portion of saturated aqueous sodium chloride solution and dried over magnesium sulfate to an oil. The oil is dissolved in ether, filtered through celite, and treated with ethereal maleic acid to form a salt. The salt is washed well with ether and recrystallized from acetone-ether to give a white powder of 3-(2,4-dichlorophenyl)-1'-[3-(4-fluorobenzoyl)propyl]-1,3-dihydrospiro[benzo(c)thiophene-1,4'-piperidine]maleate, m.p. 124°–127° C. A thrice recrystallized sample melts at 127°–129° C.

Analysis: Calculated for $C_{28}H_{26}Cl_2FNOS.C_4H_4O_4$: 60.96%C; 4.80%H; 2.22%N; 11.25%Cl. Found: 61.13%C; 4.78%H; 2.06%N; 11.02%Cl.

EXAMPLE 57

To 5.0 g of phenyl chloroformate in 80 ml of dichloromethane is added 7.89 g of the free base, 3-(3-fluorophenyl)-1,3-dihydro-1'-methylspiro[benzo(c)thiophene-1,4'-piperidine] of Example 55, in 10 ml of dichloromethane over 20 minutes. The reaction mixture is stirred at room temperature for 21 hours, then diluted with 200 ml of dichloromethane. The resultant mixture is washed with two 175 ml portions of 10% aqueous sodium hydroxide solution, two 150 ml portions of water and one 70 ml portion of saturated aqueous sodium chloride solution, and dried over magnesium sulfate to give an oil. The oil is chromatographed on silica gel with dichloromethane to give an oil, which crystallizes to yield 3-(3-fluorophenyl)-1,3-dihydro-1'-phenoxycarbonylspiro[benzo(c)thiophene-1,4'-piperidine], m.p. 134°–142° C. A portion is recrystallized twice from toluene:hexane, m.p. 144°–146° C.

Analysis: Calculated for $C_{25}H_{22}FNO_2S$: 71.58%C; 5.29%H; 3.34%N. Found: 71.60%C; 5.33%H; 3.22%N.

EXAMPLE 58

To 6.97 g of 3-(3-fluorophenyl)-1,3-dihydro-1'-phenoxycarbonylspiro[benzo(c)thiophene-1,4'-piperidine] of Example 57 in 100 ml of ethylene glycol, under nitrogen, at 150° C. is added 16 g of 85% potassium hydroxide pellets. The reaction is stirred in a 160° C. bath for 45 minutes. The solution is then poured into 225 ml of ice-water, diluted to 500 ml and extracted with three 175 ml portions of dichloromethane. The combined dichloromethane extracts are washed with 200 ml portions of water and one 50 ml portion of saturated aqueous sodium chloride solution, and dried over magnesium sulfate to give a solid free base. The free base in ether is treated with ethereal maleic acid to give a salt. The salt is washed with ether and recrystallized from methanol-acetone-ether to give a white powder of 3-(3-fluorophenyl)-1,3-dihydrospiro[benzo(c)thiophene-1,4'-piperidine]maleate, m.p. 188°–188.5° C.

Analysis: Calculated for: $C_{18}H_{18}FNS$: 63.61%C; 5.34%H; 3.37%N; 4.57%F. Found: 63.53%C; 5.37%H; 3.31%N; 4.45%F.

EXAMPLE 59

To 2.75 g (9.19 mmols) of free base 3-(3-fluorophenyl)-1,3-dihydrospiro[benzo(c)thiophene-1,4'-piperidine] of Example 58 in 47 ml of sieve-dried dimethylformamide is added 2.81 g of γ-chloro-p-fluorobutyrophenone ethylene ketal with 1.82 g of potassium iodide and 1.82 g of sodium bicarbonate. The reaction is stirred at 65°–90° C. for 20 hours; then diluted with 75 ml of chloroform, filtered, and rotary evaporated at 75° C. to an oil. The oil is partitioned between 125 ml of dichloromethane and 85 ml of water. A 10 ml portion of saturated aqueous sodium bicarbonate is added and the solutions separated. The organic layer is washed with one 80 ml portion of water and one 30 ml portion of saturated aqueous sodium chloride solution and dried over magnesium sulfate to an oil. The oil is chromatographed on alumina with ether to give 3-(3-fluorophenyl)-1'-[3-(4-fluorobenzoyl)propyl]-1,3-dihydrospiro[benzo(c)thiophene-1,4'-piperidine]ethylene ketal. Recrystallization from cyclohexane-pentane yields a sample which melts at 121.5°–123° C.

Analysis: Calculated for $C_{30}H_{31}F_2NO_2S$: 70.98%C; 6.17%H; 2.76%N. Found: 70.97%C; 6.20%H; 2.43%N.

EXAMPLE 60

To 3.75 g of 3-(3-fluorophenyl)-1'-[3-(4-fluorobenzoyl)propyl]-1,3-dihydrospiro[benzo(c)thiophene-1,4'-piperidine]ethylene ketal of Example 59 in 38 ml of ethanol is added 38 ml of 3N hydrochloric acid. The reaction is refluxed for two hours and allowed to stand at room temperature for 16 hours. The solution is diluted with 100 ml of water and a few ml of 40% aqueous sodium hydroxide solution are added to achieve a pH of 11. The mixture is then diluted with 175 ml of water are extracted with three 175 ml portions of dichloromethane solution. The combined dichloromethane extract is washed with two 125 ml portions of water and one 60 ml portion of saturated aqueous sodium chloride solution and dried over magnesium sulfate to an oil. The oil, in ether, is treated with ethereal maleic acid; and the resulting salt washed with ether and recrystallized from acetone ether to a white, crystalline powder of 1'-[3-(4-fluorobenzoyl)propyl]-3-(3-fluorophenyl)-1,3-dihydrospiro[benzo(c)thiophene-1,4'-piperidine]maleate m.p. 149°–150.5° C.

Analysis: Calculated for $C_{28}H_{27}F_2NOS \cdot C_4H_4O_4$: 66.31%C; 5.39%H; 2.42%N; 6.56%F. Found: 66.35%C; 5.54%H; 2.14%N, 6.61%F.

EXAMPLE 61

To a solution of 3.10 g of the free base 1,3-dihydro-3-(4-methylphenyl)spiro[benzo(c)thiophene-1,4'-piperidine] of Example 40 in 54 ml of dimethylformamide is added 3.21 g of the γ-chloro-p-fluorobutyrophenone ethylene ketal, 2.07 g of potassium iodide and 2.07 g of sodium bicarbonate. The reaction mixture is stirred and heated at 65°–90° C. 18 hours. The reaction mixture is diluted with 75 ml of chloroform, filtered, and evaporated to an oil. The oil is partitioned between 150 ml of dichloromethane and 125 ml of water. The organic layer is washed with water and an aqueous sodium chloride solution and then dried over $MgSO_4$. The solution is filtered and evaporated to an oil which is column chromatographed on an $Al_2O_3/Et_2O$. A sample of the resultant free base is converted to the oxalate salt of 1'-[3-(4-fluorobenzoyl)propyl]-3-(4-methylphenyl)-1,3-dihydrospiro[benzo(c)thiophene-1,4'-piperidine]ethylene ketal oxalate.

Analysis: Calculated for $C_{31}H_{34}FNO_2S \cdot C_2H_2O_4$: 66.76%C; 6.11%H; 2.36%N. Found: 66.85%C; 6.12%H; 2.32%N.

EXAMPLE 62

A solution of 2.57 g of 1'-[3-(4-fluorobenzoyl)propyl]-1,3-dihydro-3-(4-methylphenyl)spiro[benzo(c)thiophene-1,4'-piperidine]ethylene ketal of Example 61, 27 ml of absolute ethanol, and 27 ml of 3N HCl is heated on a steam bath for 45 minutes. The reaction is cooled, diluted with 75 ml of water, and taken to pH 11 using a 40% aqueous NaOH solution. The solution is diluted with 150 ml of water and extracted with dichloromethane. The $CH_2Cl_2$ fractions are combined, washed with water and brine, and dried over $MgSO_4$. The dried $CH_2Cl_2$ solution is filtered and evaporated to an oil which solidifies under pentane. The filtered product is recrystallized from ethyl acetate to give 1'-[3-(4-fluorobenzoyl)propyl]-1,3-dihydro-3-(4-methylphenyl)-spiro[benzo(c)thiophene-1,4'-piperidine], m.p. 134°–135° C.

Analysis: Calculated for $C_{29}H_{30}FNOS$: 75.78%C; 6.58%H; 3.05%N. Found: 75.61%C; 6.67%H; 3.07%N.

EXAMPLE 63

To 6.87 g of 3-(4-chlorophenyl)-1,3-dihydrospiro[benzo(c)thiophene-1,4'-piperidine] of Example 15 in a solution of 33 ml of 2-butanone with 33 ml of dimethylformamide is added 6.04 g of γ-chloro-2,4-difluorobutyrophenone ethylene ketal followed by 6.5 g of sodium bicarbonate and 4.08 g of potassium iodide. The reaction is stirred at 75°–80° C. for 18 hours, then 400 ml of ice-water is added and the mixture extracted with three 125 ml portions of ether. The combined ether extracts are washed with two 150 ml portions of water and one 30 ml portion of brine and dried over magnesium sulfate to yield an oil. The oil is chromatographed on 300 ml of alumina with ether to give an oil which eventually crystallizes to a product. A portion of the product is diluted with ether, treated with ethereal maleic acid to form the salt. The salt is recrystallized once from methanol-ether and once from acetone-ethyl acetate pentane to give 3-(4-chlorophenyl)-1'-[3-(2,4-difluorobenzoyl)propyl]-1,3-dihydrospiro[benzo(c)thiophene-1,4'-piperidine]ethylene ketal maleate, melting at 148°–149° C.

Analysis: Calculated for $C_{30}H_{30}ClF_2NO_2S \cdot C_4H_4O_4$: 62.05%C; 5.21%H; 2.13%N. Found: 61.94%C; 5.01%H; 2.16%N.

EXAMPLE 64

To 8.21 g (15.15 mmols) of free base 3-(4-chlorophenyl)-1-[3-(2,4-difluorobenzoyl)propyl]-1,3-dihydrospiro[benzo(c)thiophene-1,4'-piperidine]ethylene ketal of Example 63 in 62 ml of warm 95% ethanol is added 31 ml of 3N hydrochloric acid, slowly, to give a suspension. The reaction is stirred at room temperature for 3 hours and on a steam bath for 45 minutes. The reaction is then diluted with 400 ml of water and basified with ammonium hydroxide. The aqueous mixture is extracted with two 150 ml portions of ether and two 250 ml portions of 1:1, ether:toluene. Combined organic layers are washed with water and saturated aqueous sodium chloride solution and dried over magnesium sulfate to a brown oil. The oil is chromatographed on silica gel with ether to give a solid. A portion of the product is recrystallized thrice from ether-pentane to give 3-(4-chlorophenyl)-1'-[3-(2,4-difluorobenzoyl)propyl]-1,3-dihydrospiro[benzo(c)thiophene-1,4'-piperidine], melting at 98°–100° C.

Analysis: Calculated for $C_{28}H_{26}ClF_2NOS$: 67.52%C; 5.26%H; 2.81%N. Found: 67.25%C; 5.49%H; 2.69%N.

EXAMPLE 65

A mixture of 1,3-dihydro-3-phenylspiro[benzo(c)thiophene-1,4'-piperidine] of Example 4 (3.75 g), 3.7 g of γ-chloro-2,4-difluorobutyrophenone ethylene ketal, 2.5 g of KI, 4.0 g of sodium bicarbonate in a mixture of 20 ml DMF and 20 ml of 2-butanone is refluxed for 3 hours. The cooled mixture is diluted with water, extracted three times with ether and the washed, dried ether solution concentrated to an oily residue. The residual is purified by passing through an alumina column. Elution with ether affords the tertiary amine which is converted to a crystalline maleate of 1'-[3-(2,4-difluorobenzoyl)propyl]-1,3-dihydro-3-phenylspiro[benzo(c)thiophene-1,4'-piperidine]ethylene ketal maleate, m.p. 171°–172.5° C.

Analysis: Calculated for $C_{30}H_{31}F_2NO_2S \cdot C_4H_4O_4$: 65.47%C; 5.66%H; 5.14%S. Found: 65.21%C; 5.68%H; 5.36%S.

EXAMPLE 66

A solution of 5.0 g of the free base 1'-[3-(2,4-difluorobenzoyl)propyl]-1,3-dihydro-3-phenylspiro[benzo(c)thiophene-1,4'-piperidine]ethylene ketal of Example 65 in 20 ml of 3N HCl and 20 ml of water is allowed to stand at room temperature for 3 hours. The excess acid and solvents are removed under pressure at 60° C., the residue is basified with concentrated $NH_4OH$. The liberated oil is taken up in ether, washed and dried. Removal of solvents yields a clear oil which is converted to a crystalline maleate in ether of 1'-[3-(2,4-difluorobenzoyl)propyl]-1,3-dihydro-3-phenylspiro[benzo(c)thiophene-1,4'-piperidine]maleate, m.p. 134°–135° C.

Analysis: Calculated for $C_{28}H_{27}F_2NOS \cdot C_4H_4O_4$: 66.67%C; 5.39%H; 5.53%S. Found: 66.21%C; 5.36%H; 5.79%S.

EXAMPLE 67

To 5.60 g of the free base 1'-[3-(4-fluorobenzoyl)propyl]-3-(3-methylphenyl)-1,3-dihydrospiro[benzo(c)thiophene-1,4'-piperidine]ethylene ketal of Example 50 in 56 ml of warm ethanol is slowly added 56 ml of 3N hydrochloric acid. The reaction is refluxed for 45 minutes, then cooled to room temperature, basified with a small amount of 40% aqueous sodium hydroxide, and diluted with 350 ml of water. The solution is extracted with three 150 ml portions of dichloromethane. The combined dichloromethane extract is washed with two 200 ml portions of water, one 75 ml portion of brine and dried over magnesium sulfate to give an oil. The oil is dissolved in ether, filtered, and treated with ethereal hydrogen bromide to form a salt. The salt is washed with ether and recrystallized from methanol-acetone-ether to give a powder of 1'-[3-(4-fluorobenzoyl)propyl]-1,3-dihydro-3-(3-methylphenyl)spiro[benzo(c)thiophene-1,4'-piperidine]hydrobromide which shrinks to a gel at 190°–195° C. and melts to a dark fluid at 217°–218° C.

Analysis: Calculated for $C_{29}H_{30}FNOS \cdot HBr$: 64.44%C; 5.73%H; 2.59%N; 3.52%F. Found: 64.30%C; 5.79%H; 2.48%N; 3.56%F

EXAMPLE 68

Physostigmine Lethality in Mice

Groups of ten male CD-1 mice (18–25 gms) are utilized for a Time Response. Animals received food and water ad libitum. Drugs are prepared in distilled water. If insoluble, one drop of a suitable surfactant is added. Dose volume is 10 ml/kg.

The test compound is administered intraperitoneally (i.p.). Control group receives vehicle. At 30, 60 and 120 minutes after administration of test compound, an i.p. injection of physostigmine sulfate at 2.5 ml/kg is given to each of the animals.

One hour after each physostigmine injection the groups are checked for deaths. Surviving mice are considered protected. Of the three time periods checked, the time period with the greatest protection is the peak time of drug activity. If there are animals protected in the vehicle control group, the normalized percent protected is calculated thus:

$$\frac{\dfrac{\text{No. protected for drug}}{\text{No. in group}} - \dfrac{\text{No. protected vehicle control}}{\text{No. in group}}}{100 \times \dfrac{\text{No. protected vehicle control}}{\text{No. in group}}} \times 100\%$$

RESULTS

| Compound | Dose (mg/kg, i.p.) | Anticholinergic Activity Normalized % Protected at Peak Time |
|---|---|---|
| 1,3-dihydro-3-(4-tolyl)spiro[isobenzofuran-1,4'piperidine] | 50 | 83 |
|  | 50 | 50 |
|  | 64 | 10 |
|  | 32 | 10 |
|  | 16 | 10 |
|  | 8 | 30 |
| 1,3-dihydro-3-(4-tolyl)spiro[benzo(c)thiophene-1,4'-piperidine] | 50 | 40 |
| 1,3-dihydro-1'methyl-3-(2-tolyl)-spiro[isobenzofuran-1,4'piperidine] | 50 | 33 |
| 1,3-dihydro-1'-methyl-3-(2-tolyl)-spiro[benzo(c)thiophene-1,4'-piperidine] | 50 | 0 |
| 1,3-dihydro-3-phenylspiro[isobenzofuran-1,4'piperidine] | 25 | 44 |
|  | 10 | 44 |
| 1,3-dihydro-3-phenylspiro[benzo(c)thiophene-1,4'piperidine] | 50 | 10 |
|  | 10 | 0 |

RESULTS -continued

| Compound | Dose (mg/kg, i.p.) | Anticholinergic Activity Normalized % Protected at Peak Time |
|---|---|---|
| 1,3-dihydro-3-(4-fluorophenyl)spiro-[isobenzofuran-1,4'-piperidine] | 25 | 63 |
|  | 10 | 63 |
| 1,3-dihydro-3-(4-fluorophenyl)spiro-[benzo(c)thiophene-1,4'-piperidine] | 40 | 0 |
| 1,3-dihydro-1'-[3-(4-fluorobenzoyl)propyl]-3-(4-fluorophenyl)-spiro[isobenzofuran-1,4'-piperidine] | 25 | 0 |
| 1,3-dihydro-1'-[3-(4-fluorobenzoyl)-propyl]-3-(4-fluorophenyl)spiro[benzo(c)thiophene-1,4'-piperidine] | 50 | 0 |
| 1,3-dihydro-1'-[3-(4-fluorobenzoyl)propyl]-3-(4-methylphenyl)spiro[isobenzofuran-1,4'-piperidine] | 50 | 20 |
| 1,3-dihydro-1'-[3-(4-fluorobenzoyl)propyl]spiro[isobenzofuran-1,4'-piperidine] | 64 | 10 |
| 1,3-dihydro-1'-[3-(4-fluorobenzoyl)propyl]-5-methoxy-spiro[isobenzofuran-1,4'-piperidine] | 25 | 10 |
| 1,3-dihydro-3-(4-chlorophenyl)-1'-[3-(4-fluorobenzoyl)propyl]-spiro[isobenzofuran-1,4'-piperidine] | 25 | 0 |
| 1,3-dihydro-6-fluoro-1'-[3-(4-fluorobenzoyl)propyl]-spiro[isobenzofuran-1,4'-piperidine] | 25 | 0 |
| 1,3-dihydro-3-(2-methylphenyl)-spiro[isobenzofuran-1,4'-piperidine] | 50 | 0 |
| 1,3-dihydro-6-chloro-1'-[3-(4-fluorobenzoyl)propyl]spiro-[isobenzofuran-1,4'-piperidine] | 25 | 0 |
| 1,3-dihydro-3-(4-fluorophenyl)-1'-methylspiro[benzo(c)thiophene-1,4'-piperidine] | 50 | 78 |
|  | 40 | 17 |
|  | 64 | 0 |
|  | 32 | 0 |
| 1,3-dihydro-3-(4-chlorophenyl)-spiro[benzo(c)thiophene-1,4'-piperidine] | 50 | 0 |
| 1,3-dihydro-3-(4-chlorophenyl)-1'-methylspiro[benzo(c)thiophene-1,4'-piperidine] | 50 | 0 |
| 1,3-dihydro-3-(3,4-dichlorophenyl)-spiro[benzo(c)thiophene-1,4-piperidine] | 50 | 0 |
| 1,3-dihydro-3-(2,4-dichlorophenyl)-1'-methylspiro(benzo-(c)thiophene-1,4'-piperidine] | 50 | 0 |
| 1,3-dihydro-3-(3,4-dichlorophenyl)-1'-methylspiro[benzo(c)thiophene-1,4'-piperidine] | 50 | 0 |
| 1,3-dihydro-3-(4-chlorophenyl)-1'-(cyclopropylmethyl)-spiro-[benzo(c)-thiophene-1,4'-piperidine] | 50 | 17 |
| 1,3-dihydro-1'-methyl-3-phenyl-[benzo(c)thiophene-1,4'-piperidine] | 25 | 0 |
| 1,3-dihydro-3-(4-methylphenyl)-1'-methyl-spiro[benzo(c)-thiophene-1,4'-piperidine] | 50 | 40 |
| 1,3-dihydro-3-(3-methylphenyl)-spiro[benzo(c)thiophene-1,4'-piperidine] | 50 | 0 |

We claim:

1. A process for preparing a compound of the formula

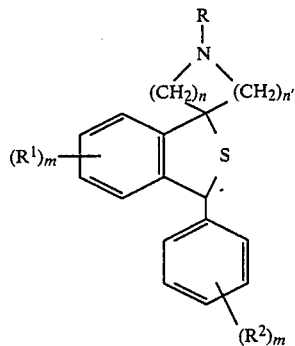

or an optical antipode or pharmaceutically acceptable salt thereof in which R is loweralkyl or phenylloweralkyl, $R^1$ and $R^2$ are the same or different and each can be hydrogen, loweralkyl, loweralkoxy, trifluoromethyl, chlorine, bromine, fluorine, methylenedioxy or loweralkylthio and m, n and n' are integers from 1 to 3; and the sum of n and n' is 3 or 4 which comprises converting a 2-bromo-fluorobenzene of the formula

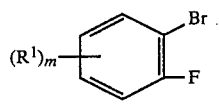

to its 2-lithio derivatives with a loweralkyllithium at a temperature ranging from −80° to −20° C., in a suitable solvent such as ether, hexane or tetrahydrofuran, reacting the 2-lithio derivative with a cycloazalkanone of the formula

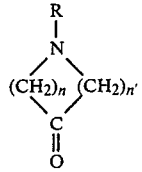

in which R is loweralkyl or phenylloweralkyl to provide a phenylcycloazalkanol of the formula

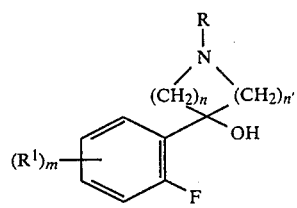

reacting the phenylcycloazalkanol with a benzylmercaptan of the formula

37
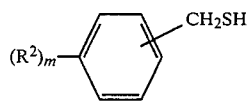
in the presence of glacial acetic acid and boron trifluoride etherate at a temperature of from ambient to 100° C. to provide a 4-benzylthio-4-phenylcycloazalkane of the formula
38
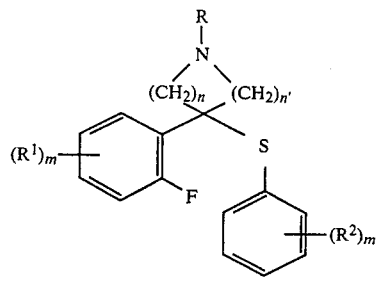
and cyclizing the 4-benzylthio-4-phenylcycloazalkane.
* * * * *